United States Patent [19]

Maggard

[11] Patent Number: 5,243,546
[45] Date of Patent: Sep. 7, 1993

[54] SPECTROSCOPIC INSTRUMENT CALIBRATION

[75] Inventor: Steven M. Maggard, Barboursville, W. Va.

[73] Assignee: Ashland Oil, Inc., Ashland, Ky.

[21] Appl. No.: 698,411

[22] Filed: Jan. 10, 1991

[51] Int. Cl.$^5$ .............................................. G06F 15/20
[52] U.S. Cl. ............................ 364/571.02; 364/571.01
[58] Field of Search ............ 250/339; 364/498, 571.01, 364/571.02

[56] References Cited

U.S. PATENT DOCUMENTS

| | | | |
|---|---|---|---|
| Re. 34,070 | 9/1992 | Regimand | 364/571.02 X |
| 3,877,818 | 4/1975 | Button | 356/186 |
| 4,800,279 | 1/1989 | Hieptje et al. | 250/255 X |
| 4,864,842 | 9/1989 | Regimand | 364/571.02 X |
| 4,866,644 | 9/1989 | Shenk et al. | 364/571.02 |
| 4,959,796 | 9/1990 | Hidaka et al. | 364/496 X |
| 4,997,280 | 3/1991 | Norris | 356/308 |
| 5,121,337 | 6/1992 | Brown | 364/578 X |

FOREIGN PATENT DOCUMENTS 0285251 2/1988 European Pat. Off. .

OTHER PUBLICATIONS

"Partial Least-Squares Methods for Spectral Analyses 1. Relation to Other Quantitative Calibrating Methods and the Extraction of Qualitative Information" by Haaland et al; The Analytical Chemistry Journal, vol. 60, No. 11, Jun. 1, 1988, pp. 1198–1202.

"Advances in Near Infrared Analyzer Technology" Dr. H. Mark & Dr. D. Kemeny, Feb. 1991 Chemical Processing, pp. 54–58.

"Multivariate Instrument Standardization", Y. Wang et al., Anal. Chem. 1991, 63, 2750–2756, vol. 63, No. 23, Dec. 1, 1991.

"Prediction of Gasoline Octave Numbers from Near-Infrared Spectral Features in the Range 660–1215 nm", Kelly et al., Anal Chem., vol. 61, No. 4, Feb. 15, 1989, pp. 313–320.

"Determination of Carbon-Hydrogen Groups in High Molecular Weight Hydrocarbons", A. Evans and R. R. Hibbard, Analytical Chemistry, vol. 23, No. 11, Nov. 1951, pp. 1604–1610.

*Primary Examiner*—Edward R. Cosimano
*Attorney, Agent, or Firm.*—Richard C. Willson, Jr.; Stanley M. Welsh

[57] ABSTRACT

A calibrated spectrometer can indirectly determine a physical or chemical property of a sample based upon spectral responses measured by the spectrometer with respect to the particular sample. This invention is directed to a method for calibrating or recalibrating a first spectrometer in light of a second spectrometer, or itself, respectively. The calibration employs a unique selection and manipulation of spectral data obtained from both the first and the second instrument. The recalibration employs a unique selection and manipulation of spectral data from the same first instrument, that is obtained both before and after the need for recalibration arises. Instead of modifying the respective responses of the first and second instrument, or the first instrument before and after the need for calibration arises, this invention modifies the calibration equation of the second, or recalibrated instrument, to yield consistent results to those obtained by the first instrument, or the first instrument before it goes out of calibration. A calibration equation is an equation which transforms spectral data of a particular sample at a variety of wavelengths to a calculated value for a chemical or physical property. Generally, the form of such calibration equations is that of a linear combination of absorbances or mathematical transforms of absorbances measured by the first and second instrument for each sample. The accuracy of the calibrated or recalibrated instrument is maintained and in some instances improved.

79 Claims, 3 Drawing Sheets

SPECTROSCOPIC INSTRUMENT CALIBRATION

BACKGROUND OF INVENTION

I. Field of the Invention

This invention relates to spectrophotometers capable of measuring electromagnetic radiation, such as infrared, near-infrared, ultraviolet, visible, Ramon spectra, Rayleigh scattering, and the like. More specifically, this invention relates to calibration techniques useful for predicting chemical or physical properties based on observed spectral data, preferably data obtained by means of a spectrophotometer. Still more preferably, this invention embodies near-infrared calibration equations suitable for making predictions or estimates of physical or chemical properties such as octane.

II. Prior Art Summary

In J. Sci. Food Agric., 34(1983), p. 1441-1443, B. G. Osborne directly transfers a calibration equation from one instrument to another.

*Use of Indirect Multivariate Calibration for Quality Control of Agricultural Products by Near-Infrared Spectroscopy*, G. Puchwein and A. Eibelhuber (Mikrochim. Acta (Wien), 1986 II, 43-51) teach a computer program for calibrating an instrument. The program picks relevant frequencies for spectral data for part of a set of samples with which to calibrate an instrument and then validates with respect to the remaining samples.

*Near-Infrared Limitations to Silicon Photodetector Self-Calibration*, J. M. Palmer (SPIE Vol. 499, Optical Radiation Measurements [1984], p. 7-14) teaches self-calibrating silicon photodiode detectors.

*A Simple Internal Modulation Technique for the Spectral Calibration of Circular Variable Filter Spectrometers in the Near-Infrared*, Chandrasekhar, Ashok, Bhatt, and Manian (Infrared Physics, Volume 24, No. 6, 1984, p. 571-572) teach the wavelength calibration of telescopes attached to near-infrared instruments for astronomical studies using the frequency dependent signal of a low-pressure mercury arc lamp.

Mark and Workman (Spectroscopy, 311), 28) developed a computer algorithm to find isonumeric wavelengths. Isonumeric wavelengths are calibration wavelengths which yield the same absorbance readout on a master NIR and a slave NIR. These wavelengths therefore do not change substantially from one instrument to another.

Heckman, Diffee, and Milhous (Analytica Chemica Acta, 192(1987), 197) teach a computer program that transfers calibration equations by computing slope and bias corrections for each wavelength in the equation. This method of slope and bias corrections is, in fact, used in Example 3 of this application. In U.S. Pat. No. 4,761,522 R. D. Rosenthaul claims a poly-tetrafluoroethylene standard for near-infrared and processes for making that standard. That standard, however, is not used in calibration transfer from one instrument to another.

B. G. Osborne, in an article entitled, *Calibration of Instrument for Near-Infrared Spectroscopy*, (48 Spectroscopy, Vol. 4 No. 4, p. 48-55). Osborne discloses in detail the steps for establishing simple correlations by multiple linear regression and also the use of derivatives of linear terms. Validation of calibration curves are discussed; specifically how particular wavelengths are chosen to establish the terms in the multiple linear regression equations, along with the statistical significance of a particular calibration sample. This method can be utilized in this invention for the purpose of defining the calibration equations of the calibrated instrument for a range of values within which useful predictions can be made, i.e., the range of interest.

Still other methods for determining calibration equations are those discussed in Analytical Chemistry Journal Vol. 60, pages 1193-1202 (1988) by David M. Haaland and Edward V. Thomas. The principles of inverse least squares, partial least squares, classical least squares, and principal component regression analysis are disclosed. More specifically, for purposes of the following discussion, assume: capital letters in boldface identify matrices, small letters in boldface identify column vectors, small letters in italics identify scalers, and any primes used in conjunction with boldface letters signify a transposition.

Using the notation just discussed and the following assumptions: a Beer's law model for m, calibration standards containing l, chemical components with a spectra of n, digitized absorbances, the following equation in matrix notation holds:

$$A = CK + E_A \qquad \text{Equation (1)}$$

where A is the m×n matrix of calibration spectra, C is the m×l matrix of component concentrations, K is the l×n matrix of absorptivity—path length products, and $E_A$ is the model. K then represents the matrix of pure-component spectra at unit concentration and unit path length. The classical least-squares solution to Equation 1 during calibration is:

$$\hat{K} = (C'C)^{-1}C'A \qquad \text{Equation (2)}$$

where $\hat{K}$ indicates the least-squares estimate of K with the sum of squared spectral errors being minimized. During prediction, the least-squares solution for the vector of unknown component concentrations, c, is:

$$\hat{c} = (\hat{K}\hat{K}')^{-1}\hat{K}a \qquad \text{Equation (3)}$$

where a is the spectrum of the unknown sample and $\hat{K}$ is from Equation 2.

Equation 1 shows that CLS can be considered a factor analysis method since the spectral matrix A is represented as the product of two smaller matrices C and K. The pure-component spectra (rows of K) are the factor loadings (also called loading vectors) and the chemical concentration (elements in C) are the factors (or scores). This model changes the representation of the calibration spectra into a new coordinate system with the new coordinates being the l pure-component spectra rather than the n spectral frequencies. Although this coordinate system is not necessarily orthogonal, it has the advantage that the l spectral intensities for each mixture in this new coordinate system of pure-component spectra are the elements of C; i.e., the intensities in the new coordinate system are the component concentrations. This is clear when one considers that the component concentrations represent the amount (or intensities) of the pure-component spectra which make up any given mixture spectrum.

Since CLS is a full-spectrum method, it can provide significant improvements in precision over methods that are restricted to a small number of frequencies, allow simultaneous fitting of spectral base lines, and make available for examination and interpretation least-squares estimated pure-component spectra and full-spectrum residuals.

The inverse-least square ("ILS") method assumes concentration is a function of absorbance. An inverse Beer's law model for m, calibration standards with spectra of n digitized absorbances is given by:

$$C = AP + E_c \qquad \text{Equation (4)}$$

where C and A are as before, P is the $n \times 1$ matrix of the unknown calibration coefficients relating the l component concentrations to the spectral intensities, and $E_c$ is the $m \times 1$ vector of random concentration errors or residuals that are not fit by the model. Since model error is presumed to be error in the component concentrations, this method minimizes the squared errors in concentrations during calibration. The inverse representation of Beer's law has the significant advantage in that the analysis based on this model is invariant with respect to the number of chemical components, l, included in the analysis. If it is assumed that the elements in different columns of Ec are independent, an identical analysis for each individual analyte can be obtained by considering the reduced model for one component:

$$c = Ap + e_c \qquad \text{Equation (5).}$$

Here is the $m \times 1$ vector of concentrations of the analyte of interest in the m calibration samples, p is then an $n \times 1$ vector of calibration coefficients, and $e_c$ is the $m \times 1$ vector of concentration residuals not fit by the model.

During calibration, the least-squares solution for p in eq 5 is:

$$\hat{p} = (A'A)^{-1} A'c \qquad \text{Equation (6).}$$

During prediction, the solution for the analyte concentration in the unknown sample is simply:

$$\hat{c} = a'\hat{p} \qquad \text{Equation (7).}$$

This means a quantitative spectral analysis can be performed even if the concentration of only one component is known in the calibration mixtures. The components not included in the analysis must be present and implicitly modeled during calibration. The above capability of the ILS method has resulted in it being used for near-infrared analysis ("NIRA") methods.

Partially squares ("PLS") and principal component regression ("PCR") are both factor analysis methods with many of the advantages of the CLS method. Using the spectral decomposition notation of Lindberg, et al, Anal. Chem. 1983, 55, 643, the calibration equation can be represented for either a principal component analysis ("PCA") or PLS model as follows:

$$A = TB + E_A \qquad \text{Equation (8)}$$

where B is a $h \times n$ matrix with the rows of B being the new PLS or PCA basis set of h full-spectrum vectors, often called loading vectors or loading spectra. T is an $m \times h$ matrix of intensities (or scores) in the new coordinate system of the h PLS or PCA loading vectors for the m sample spectra. In PCA the rows of B are eigenvectors of $A'A$, and the columns of T are proportional to the eigenvectors of $AA'$. $E_A$ is now the $m \times n$ matrix of spectral residuals not fit by the optimal PLS or PCR model. The analogy between eq 8 of PLS or PCA and eq 1 for CLS is quite clear since both equations involve the decomposition of A into the product of two smaller matrices. However, now rather than the basis vectors being the pure-component spectra, they are the loading vectors generated by the PLS or PCA algorithms. The intensities in the new coordinate system are no longer the concentrations as they were in CLS, but they can be modeled as linearly related to concentrations as shown later. The new basis set of full-spectrum loading vectors is composed of linear combinations of the original calibration spectra. The amounts (i.e., intensities) of each of the loading vectors which are required to reconstruct each calibration spectrum are the scores.

In general, in a noise-free system only a small number of the full-spectrum basis vectors are required to represent the calibration spectra (A). When the rank of A which is important for concentration prediction is r, then the optimal PLS or PCR model in eq 8 will have the dimension h equal to r. In general $r < m$ and $r < n$, in which case PLS and PCA will have reduced the number of intensities (n) of each spectrum in the spectral matrix A to a small number of intensities (r) in the new coordinate system of the loading vectors. This data compression step also reduces the noise (32) since noise is distributed throughout all loading vectors while the true spectral variation is generally concentrated in the early loading vectors.

The spectral intensities (T) in the new coordinate system can be related to concentrations with a separate inverse least-squares analysis using a model similar to eq 5. However, rather than solving eq 5 by least-squares methods with the problem of calculating $(A'A)^{-1}$, we solve the following set of equations by least squares:

$$c = Tv + e_c \qquad \text{Equation (9)}$$

where v is the $h \times 1$ vector of coefficients relating the scores to the concentrations and T is the matrix of scores (intensities) from the PLS or PCA spectral decomposition in eq 8.

In conclusion, PLS and PCR are both involved in an inverse lease-squares step (PCR is simply PCA followed by the separate regression step for the model given in equation nine).

Although PCA and PLS are similar, the methods to accomplish the goals of spectral decomposition and concentration prediction are different. Both methods as implemented here involved stepwise algorithms which calculate the B and T matrices one vector at a time until the desired model has been obtained. In general, different T and B matrices are generated by the PLS and PCA methods. In PCA, the columns of T are orthogonal and the rows of B are orthogonal while in the version of PLS presented here only the columns of T are orthogonal. The PCA algorithm used here is the NIPALS (nonlinear iterative partial least-squares) algorithm developed by Wold, H. *Multivariate Analysis*; Krishnalah, P. R., Ed.; Academic: New York, 1966; page 391. NIPALS is an efficient iterative algorithm which extracts the full-spectrum loading vectors (eigenvectors of $A'A$) from the spectra in the order of their contribution to the variance in the calibration spectra. After the first loading vector has been determined, it is removed from each calibration spectrum, and the process is repeated until the desired number of loading vectors has been calculated. The potential problem with PCR is that the loading vectors which best represent the spectral data may not be optimal for concentration prediction. Therefore, it would be desirable to derive loading vectors so that more predictive information is placed in the first factors. The PLS algorithm presented here is a modification of the NIPALS algorithm, and it achieves the above goal by using concentration information to obtain the decomposition of the spectral matrix A in eq 8. Concentration-dependent loading vectors are generated (B) and the computed scores (T) are then related to the concentrations or concentration residuals after each loading vector is calculated. Therefore, in principle, greater predictive ability is forced into the early PLS loading vectors.

*Liquid Absorption Standards For Ultraviolet, Visible, and Near-Infrared Spectrophotometry*, R. G. Martinek, J. Amer. Med. Technol. July-August, 1978, on p. 210–216. Liquid absorbance standards are shown to have the following desirable characteristics: broad absorption peaks; wide wavelength range; high molar absorptivity; stability in solution; readily definable specifications of purity; and minimal spectral temperature coefficients. The purpose of using such standards is to permit calculation of absolute absorbance based upon the observed absorbance and the application of an instrument correction factor.

*The Use of Statistics In Calibrating and Validating Near Infrared On-Line Analyzers*, Bruce Thompson, ISA, 1989 Paper #88-0116, uses near-infrared for both process control and statistical process control.

*Calibration of Instruments for Near-Infrared Spectroscopy*, B. G. Osborne (Spectroscopy, 4(4), p. 48–50) teaches the need for multiplicative scattering correction for solid samples due to particle-size differences in solids and computer transfer of complex equations. Osborne discusses procedures for developing calibration equations of particular relevance and usefulness in the present invention. The selection of appropriate wavelengths and samples are discussed and relevant articles cited further explaining the techniques employed. The transfer of calibration equations from one instrument to another are disclosed to require, in the case of most modern instruments, only a change in intercept value, and computerized procedures allow for differences between spectral data generated by different instruments. These computerized procedures are not taught in detail, but are likely to involve transforming the spectral data of one instrument to be consistent with that of another instrument. This is to be distinguished from the method involved in the present invention, which instead of transforming the spectral data, the relevant coefficients in the calibration equation for the second instrument are changed from those found in the calibration equation of the first instrument in accordance with a unique procedure discussed in this specification.

In the inventor's doctoral dissertation, *A Chemometric Analysis of a Magnetic Water Treatment Device* available from University Microfilms International, Dissertation Information Service, order number 8919928, there is a discussion of linear regression analysis (simple and multiple) for a linear regression model, and data transformations which can transform non-linear types of data into data which is appropriate for linear regression modeling. Definitions are shown which establish the degree of reliability that the value of one variable (the dependent variable) can be estimated on the basis of values for other variables (the independent variables). In general, the methods for determining regression constants (or coefficients) for the calibration equations discussed in the inventor's doctoral thesis are useful in establishing the calibration equation for the first or reference instrument in the present invention.

*A New Approach to Generating Transferable Calibrations for Quantitative Near Infrared Spectroscopy*, H. Mark and J. Workman, Spectroscopy Volume 3, No. 11, p. 28–36, shows that instrument variability makes transfer of calibrations between instruments difficult. However, by selecting the wavelengths and corresponding spectral properties for such wavelengths to meet certain criterion, many of the variations between instruments will not change significantly the calibration equation from one instrument for that calibration equation which would work satisfactorily in another instrument. Not disclosed is how to revise one calibration equation from one instrument to be suitable for use in another instrument where there is a significant change in the calibration equation suitable for the second instrument.

*Tobacco constituents to Tilting Filter Instruments*, R. A. Heckman, J. T. Diffee, L. A. Milhous, Analytica Chemica Acta, 192(1987) p. 197–203, teach transferring a near-infrared monochromatic calibration for tobacco constituents to a tilting-filter instrument in order to utilize the experimental calibration equation for a sensitive but not rugged laboratory instrument to analyze data in a rugged production oriented instrument to predict properties such as moisture, glycerin, propylene glycol, nicotine, and reducing sugar. A program called MTRAN cannot be used without difficulty unless care was exercised to insure that the tilting-filter instrument is properly configured with filters so as to accommodate the wavelengths in the primary or master calibration equation for the laboratory instrument. Consequently, before the primary calibration can be transformed, the monochromatic data files are compressed to simulate a tilting-filter instrument. The resulting data file is used to re-establish the calibration equation. With the foregoing changes, CALTRAN, a program formerly used only for calibration transfer between filter instruments, could be used to effect transfer from a near-infrared monochromatic instrument to a tilting filter instrument.

Typically, the prior art seeks to make changes in the observed spectra (or mathematical transform thereof) produced in one instrument conform to those produced by a calibrated reference instrument. Only after the spectra from an uncalibrated instrument is brought into coincidence with that spectra from a calibrated instrument did one seek to transfer a calibration equation from one instrument to another. Our experience has been that this tends to introduce errors, uncertainty, and numerous numerical difficulties which reduce the ease and precision that is made possible by the invention of this specification.

U.S. Pat. No. 4,963,745 to Maggard entitled *Octane Measuring Process and Device* discloses how to initially establish a calibration equation for a reference instrument. Specifically disclosed is that spectral features, such as second derivatives, of infrared spectral data at methyne band frequencies, in the range of about 1200 to 1236 nanometers (nm), were highly correlatable to octane values for gasoline-like substances. Numerous patents and articles are cited within the text of the specification, as references cited, and as other publications, all of which including those expressly cited are expressly incorporated herein by reference.

Most methods using calibration samples, seek to place one instrument in substantially the same condition as that of another so as to produce substantially identical spectral responses. With substantially identical spectral outputs, identical inferences are then drawn.

An example of a linear calibration equation is one of the form $Y_c^i = A^i + \Sigma_j B_j^i X_{jc}^i$ where a $Y_c^i$ is the predicted value of some physical or chemical property, such as octane values for a gasoline, C, of a set called sample-c. As discussed in Example 7, 226 gasoline samples were measured to determine $A^i$, and each $B_{jc}^i$ for $j=1$ to 3, to obtain a multiple regression equation suitable for predicting pump octane values of gasoline samples, using a first instrument; instrument-i, the reference instrument. Pump octane is the average of ASTM methods D2699 and D2700, and is commonly known as $(R+M)/2$ octane. The inferred reproducibility of this test method is a 95% confidence limit of $\pm 0.71$ octane numbers over the octane range of 84–94 pump octane. From the second instrument, instrument-k, while in transflectance mode, gasoline absorbances at 1196, 1220, and 1236 nanometers (nm) were used to determine the values for the second derivative of an absorbance spectra, the spectral features, $X_{jc}^k$, in the linear calibration equation for inferring a pump octane. The standard error of prediction ("SEP") is the statistical parameter that equals the square root of the mean residual variance of unknown samples.

SUMMARY OF THE INVENTION

Figure 1:
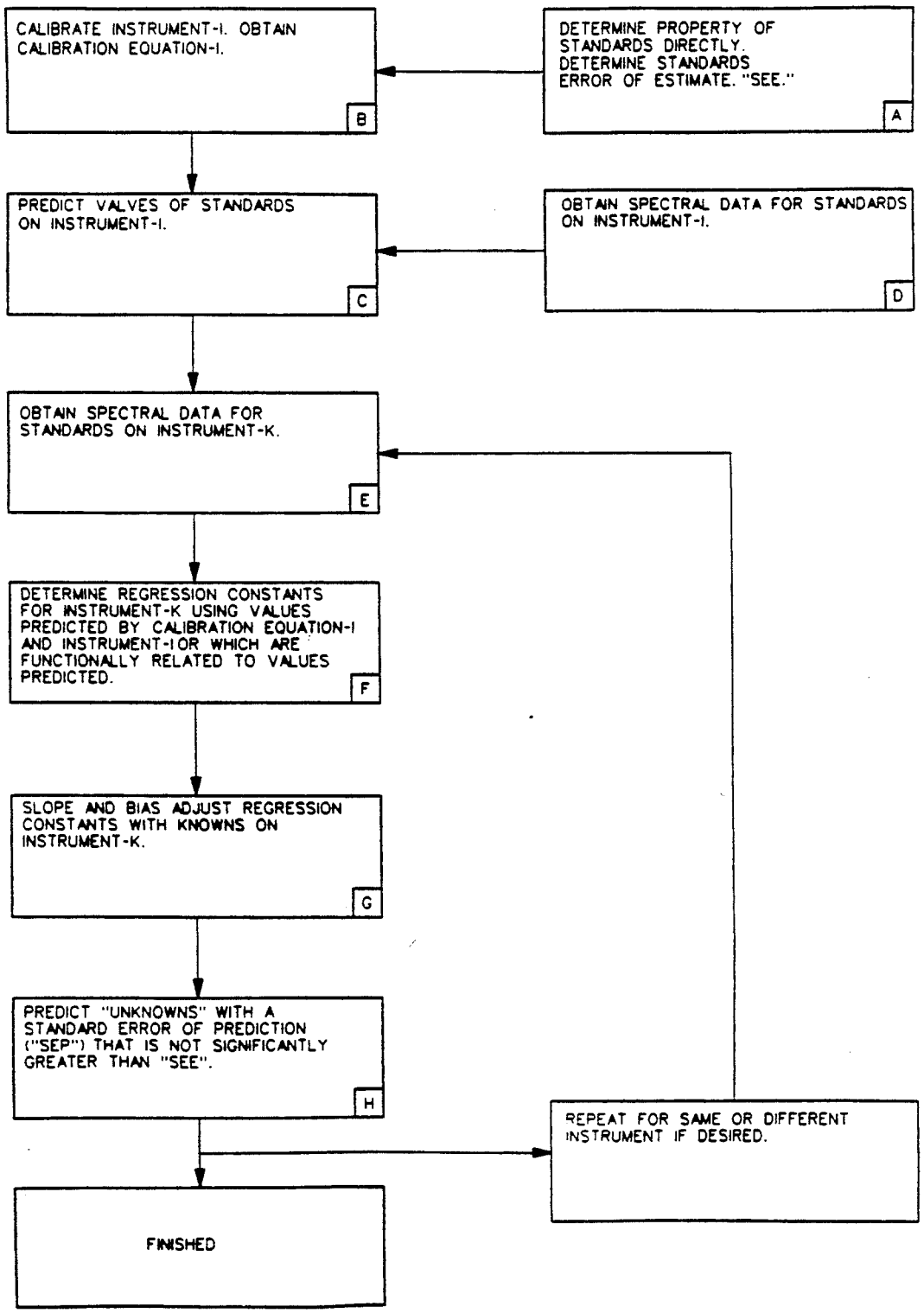
FIG. 1 is a schematic overview of this invention.

This invention solves the problem of how to utilize the results of calibrating one instrument for calibrating a different instrument. Alternatively, this invention can deal with recalibration of an instrument to insure consistent results after there has been some change in an instrument's spectral response, such as occur due to changes in light sources, for example due to replacing burned out bulbs, or due to new connections used to collect data from different sources, such as changes in fiber optics used to transmit light or electromagnetic radiation from one location to another, due to changes in path length, or due to changes in spectroscopic mode, such as from transmittance to transflectance.

The invention broadly deals with calibrating a new instrument by recourse to a reference instrument, but also contemplated is a method for continuously monitoring an instrument to be sure that it has not changed so much so that a new calibration equation is required to obtain reliable predictions for some physical or chemical property of a material of interest.

The invention contemplates methods for indirectly determining a variety of properties-p such as cetane, octane, aromatic-naphthene-olefin content, viscosity-index, molecular weight, and many others, by means of spectroscopic data. Spectral data broadly is intended to include, but not be limited to, all intensity versus wavelength spectra that arise when light, broadly intended to cover a wide range of frequencies such as radio frequency to ultra-violet interacts with a material. Generally, any spectral features (as defined in this specification) derivable from spectral data, which can be correlated to predict values for a chemical or physical property determined directly or indirectly, are within the intended scope of this invention.

Some benefits made available by this invention include:

1. Only a small number of samples (compared to the number used in the original calibration of the reference instrument) is required to determine the calibration equation for the uncalibrated instrument because the calibration equation of the reference instrument can be used. Example 7 shows that a small calibration sample consisting of only four members can be used.

2. The calibration set, sample-c, does not have to contain any unstable exemplars that may have been included in the original calibration set of samples and preferably, in the case of mixtures, such as gasoline or other petroleum fuels, can contain some of the pure components.

The limitation on appropriate members of sample-c in determining a calibration equation appropriate to an uncalibrated instrument based upon its spectral responses depends in part upon the statistical treatment chosen for the data. For multiple linear regressions, the number of members of sample-c must be at least one more than the number of wavelengths (independent variables) used in the model. For example, at least four samples must be used to transfer a calibration equation having three independent variables.

Preferably, for the reference set (sample-c) to be useful for transferring the statistical variance, co-variance, or function derived from variance from a calibrated instrument to an uncalibrated instrument, or to the same instrument at a later date, the sample-c should disclose spectral features which change as the instrument changes. For purposes of this invention, sample-c should be selected so its absorbance shows changes at the wavelengths of interest when changes in instrument performance occur, but should remain constant (within instrumental limits) when the instrument is operated at standard or typical conditions.

A specific application of one solution derived from this invention is the calibration of a near-infrared spectrophotometer by use of the results derived from a fully or partially calibrated reference near-infrared spectrophotometer. Throughout the specification, reference will be made to one or more spectrophotometers. The fully or partially calibrated spectrophotometer or other instrument will be referred to as the "reference instrument" or "reference spectrophotometer", has its calibration equation fully or partially defined. The instrument to be calibrated with respect to the reference will be referred to as the "uncalibrated instrument" or "uncalibrated spectrophotometer". A reference instrument may become uncalibrated or go out of calibration as a result of a variety of changes either within the instrument itself or from connections between the instrument and the source from which it derives its measurements or spectral data.

This invention enables an uncalibrated spectrophotometer to be calibrated by reference to a reference spectrophotometer by means of a far smaller calibration set of samples (the calibration set of samples) than was required to fully define a calibration equation for the reference spectrophotometer to begin with. The calibration set of samples is here referred to as set of sample-c, or simply, sample-c. To determine a calibration equation for calculating octane, aromatics, olefins, polyols, hydroxyl number, etc., for a near-infrared instrument, such as NIR Systems Model 6500, LT Industries Model 1200, Guided Wave Model 300 Series; Bran-Luebbe Infralyzer; or Infraprover; approximately 200 blends are used. Unfortunately, since gasolines are blends with components having different volatilities, it is very difficult, if not impossible, to store these samples to be run on an uncalibrated spectrophotometer at some later date. In other words, the samples used to calibrate the reference spectrophotometer need not be available. Not using the same materials used to calibrate the reference spectrophotometer compounds the difficulty of calibrating an uncalibrated spectrophotometer because each member of the set of sample-s of the approximately 200 had to have its octane or knock values determined in accordance with ASTM D2699 and D2700, or the like. The procedure for determining knock values are very time consuming and require multiple determinations on the same sample with different engines before reliable knock-value results are obtained.

Unknown prior to this invention was whether pure gasoline-like components that are readily reproducible could be selected for the set of sample-c. We have found in the case of near-infrared having wavelengths in the range 800 to 2500 nm (nanometers), that a preferred set of sample-c comprising: benzene; methyl t-butylether; iso-octane; n-decane; 1-octene; 2,3,4-trimethylpentane; n-heptane; cyclohexane; n-hexane; or toluene; when measured in both a reference instrument and an uncalibrated instrument to produce spectral data from each instrument, that provide sufficient data or information to calibrate the uncalibrated instrument. A calibrated instrument for purposes of this specification is one that provides stable and reproducible spectral responses and has a calibration equation by which statistically significant values for physical or chemical properties of a sample can be inferred with an accuracy equal to or exceeding the accuracy of a direct test method (e.g., ASTM) for determining such chemical or physical property.

Broadly, to transfer a calibration equation for octane, any compounds that are near-infrared active, i.e. absorb near-infrared radiation, in 800 nm to 2,500 nm can be used. Examples of such compounds are: n-paraffins, iso-paraffins, aromatics (such as dichlorobenzene or benzene) alcohols (such as methanol or ethanol), olefins (such as 1-octene), halogenated alkanes (such as trichloroethane), ketones (such as methyl ethyl ketone), ethers (such as methyl-t-butyl ether), esters (such as amylacetate), and naphthenes (such as cyclohexane, and methyl cyclohexane). Throughout this specification and claims, standard error of estimate or prediction are all at a 68% confidence limit, unless expressly stated otherwise. Each is respectively referred to also as "SEE" and "SEP".

The calibration equation for a particular instrument predicts a physical or chemical property based on spectral responses or spectral data. When measuring octane values, the particular spectral responses or mathematical transforms correspond to values of the spectral features that are selected for predicting octane values for a particular sample and are explained in detail in U.S. Pat. No. 4,963,745. The equation is preferably linear, but non-linear equations may also be used.

Spectral features are functionally related to spectral data, in that each spectral feature is uniquely defined by such spectral data. An example of such functional relations are mathematical transforms such as derivatives of first, second, and higher order; fourier analysis yielding frequency components and their contributions; difference spectra; integration by segments; and the like. The only limit on choosing such functional relations or mathematic transforms is that any values derived by applying them to spectral data must be correlatable as independent variables to accurately determine the value for a dependent variable in the calibration equation which corresponds, directly or indirectly, to the value for a physical or chemical property.

In discussing the invention in detail, the following definitions will be helpful. A "function" for purposes of this application is a correspondence that associates with each set of values for a set of independent variables, a unique value for a dependent variable. In accordance with this definition, a "calibration equation" of this invention is a function that establishes a correspondence between independent variables having values determined by spectral features, and a dependent variable that corresponds to the value for a chemical or physical property. Any function that determines values for a spectral feature that are both uniquely associated with spectral data and can be used in a calibration equation is within the scope of the invention. Spectral data are uniquely defined by the results of measuring spectral responses of a material to electromagnetic radiation. Examples of electromagnetic radiation have been discussed in other portions of this specification. The prior art has established a variety of functions that can be used to derive values for spectral features from spectral data. So long as there exists a calibration equation which contains independent variables equal to the spectral features, defined by a function, there are no limitations as to the particular spectral features or functions for spectral data that determine such spectral features which can be employed with the invention.

"Calibration equation" for purposes of this specification and claims means an equation that predicts directly or indirectly; e.g., is functionally related to, the amount of a chemical or physical property (the dependent variable) based on one or more spectral features (the independent variables(s)) and perhaps some other parameters; e.g., temperature.

"Spectral features," for purposes of this application, means absorbance, transmittance, reflectance (diffuse, specular, total, attenuated total, etc.), emission, fluorescence, phosphorescence, or transflectance, or mathematical functions thereof such as derivatives, ratios, fourier transforms, and differences for ultraviolet, visible, near-infrared, mid-infrared, far-infrared, microwave, or radio frequency electromagnetic radiation.

This invention provides a means for determining a calibration equation for a primary instrument that takes advantage of a substantial amount of work previously expended to obtain a calibration equation for a reference spectrophotometer. The primary instrument may, in fact, be the reference spectrophotometer that has gone out of calibration for reasons that have already been discussed.

To make the discussion easier to understand, the following conventions will be followed. The independent variables appropriate to a calibration equation for a primary instrument will be identified by "—i," e.g., independent variable-i corresponds to the one or more members of a set of independent variables that are contained within the calibration equation, calibration equation-i, for the primary instrument, referred to throughout as instrument-i. In most examples, there are three wavelengths used, each wavelength is referred to as wavelength-j, from which three independent variables-i derive values functionally from spectral responses of a sample, c, taken from a set of samples referred to as sample-c. Corresponding to a particular set of independent variables-i, there is a dependent variable which will be referred to as dependent variable-i. The value of dependent variable-i will usually be equal to a predicted value of property-p of sample, c. Dependent variable-i corresponds to that dependent variable found in calibration equation-i. The constants in calibration equation-i are referred to as constants-i. There are two different types of constants-i. One corresponds to a slope constant-i, and the other to a bias constant-i. The slope constants-i are coefficients of the independent variables-i. Clearly, there is a slope constant-i for each independent variable-i which is in turn dependent upon the number of wavelengths-j that are used in the calibration equation-i. There is only one bias constant-i which is not a coefficient of any independent variable-i.

When one determines a calibration equation appropriate to instrument-k by recourse to the calibration equation for instrument-i, one essentially determines a new set of calibration equation constants that correspond to constants-k. New constants are found in at least one and preferably two steps, assuming that one already has a calibration equation-i already determined for instrument-i.

To successfully transfer or modify calibration equation-i into calibration equation-k, the SEE or SEP of values for property-p based upon spectral data of instrument-k by means of calibration equation-k should most preferably be substantially as good as that achieved by instrument-i and calibration equation-i or alternatively be substantially as good as that which would be achieved had instrument-k been calibrated the same way as instrument-i, but in most cases be at least equal or better than the SEE for the primary test method for directly measuring values for property-p used to calibrate instrument-i. The benefit made available by this invention is that the number of samples that must be run on either instrument-i or instrument-k, or both, is significantly less than that number of samples required to obtain a reliable calibration equation-i for instrument-i or to fully calibrate instrument-k in the same way as instrument-i. In other words, whatever the value, E(k), in the standard error of prediction for the value for a property-p based upon instrument-k and calibration equation-k will not be substantially greater than the value for the standard error of prediction resulting from determining values for a property-p by the direct or primary test method initially used to calibrate instrument-i.

One way, but not the only way, to transfer calibration equation-i to instrument-k, is to change the constants of calibration equation-i. These changed constants become constants-k. Calibration equation-i is preferably transformed into calibration equation-k, in two steps. Step Two (below) is optional, but preferable depending upon whether the correction indicated by step two is significant. By significant, is meant the inferred variance in predicted values is not more than about 10% greater than SEE or SEP, whichever is the greater, achieved by calibration equation-k without Step Two.

Step One: Determining calibration equation-k by means of calibration equation-i involves the following sub-steps:

(a) Determine calibration equation-i by measuring dependent variables-i directly by a primary test method with a standard error of estimate of E, (See FIG. 1, Box A) and correlating said dependent variable-i to a set of independent variables-i (See FIG. 1, Box B).

The set of independent variables-i may consist of one or more members.

(b) Obtain respectively with instrument-i and instrument-k spectral data-i (See FIG. 1, Box D) and spectral data-k, (See FIG. 1, Box E) respectively, for each member of sample-c, which are to be used in step (c) (comprising at least one member, c); functionally determine value-k and value-i, respectively, (equal to each spectral feature-k and -i, respectively) for each member of sample-c corresponding to each independent variable-k and -i, respectively.

(c) Determine (in accordance with calibration equation-i) a value for said dependent variable-i for each member of sample-c (See FIG. 1, Box C). The value determined for dependent variable-i or a value determined by some function-f using that value determined for dependent variable-i is inserted into calibration equation-k for the value of dependent variable-k in calibration equation-k. Also insert into calibration equation-k the values for spectral features-k determined for each member of sample-c. (Recall that spectral features-k are functionally determined by spectral data-k that is determined from measurements made by instrument-k of each member of sample-c (See FIG. 1, Box F). The only unknowns in calibration equation-k will therefore correspond to the constants-k.) The values for constants-k that are to be substituted into calibration equation-k produce a resulting calibration equation-k, wherein the sum of all absolute differences between each estimated value of property-p for sample, c, corresponding to dependent variable-k for sample, c, and that estimated value of property-p for sample, c, corresponding to dependent variable-i for sample, c, is minimized (See FIG. 1, Box F) so that values for property-p for sample-u that have values for property-p within the range of interest are inferred based upon the resulting calibration equation-k, with an SEP of not substantially greater than the SEE or SEP of E for determining dependent variable-u directly by some primary test method (See FIG. 1, Box H). Once one has defined the constants-k, that permits one to infer the value of dependent variables-k for members of sample-u, having values for property-p, within the range of interest, within the SEE or SEP of E of the direct or primary test method, then one has obtained a calibration equation-k in light of the former calibration equation-i (See FIG. 1, Box H). An absolute difference is the value for a difference between two numbers that results from first squaring and then taking the positive square root. (Recall that instrument-k, the primary instrument, may in fact be the reference instrument that has gone out of calibration, or it may in fact be a totally different instrument).

The value for dependent variable-i (See FIG. 1, Box F) that is to be inserted into calibration equation-k for dependent variable-k can be functionally related to dependent variable-i by a function-f such as for example a logarithm (log) of any base (e.g., natural or base 10) such as $Y_c^k = \log Y_c^i$ or as a linear function, $Y_c^k = n \cdot Y_c^i + m$, where n and m are constants, or a linear combination of these; or in general, any function such as a polynomial or geometric series; provided that over the range of values of interest for $Y_s^k$, the function is substantially linear.

The range of values of interest for $Y_s^k$ is that range of values for a chemical or physical property that calibration equation-k in conjunction with instrument-k have been calibrated to predict with an SEE or SEP of less than that SEE or SEP of the primary test method (See FIG. 1, Box H).

Clearly, if $n=1$ and $m=0$, then $Y_c^k = Y_c^i$. However, for any other values of n and m, the corresponding constants will be related to those otherwise determined for $n=1$ and $m=0$ as follows:

$$A^k = nA_o^k$$

$$B_j^k = nB_{jo}^k$$

where $A_o^k$ = value of constant for $n=1$ and $m=0$ and
$B_{jo}^k$ = value of constant for $n=1$ and $m=0$ at wavelength-j In other words, whatever values for n and m that are used, the dependent variable-k will be functionally related to dependent variable-i. To determine the value for the corresponding physical or chemical property directly measured, one merely transforms inversely from $Y_c^k$ to $Y_{co}^k$ where for any m and n, except $n=0$, $Y_{co}^k = (Y_c^k - m)/n$;

Instrument-k and its spectral data are useable in this invention, if instrument-k could be calibrated by an identical method to that which could be used to successfully calibrate instrument-i.

Preferably, calibration equation-i and calibration equation-k are linear. In the generalized method discussed above for this invention, calibration equation-i and -k need not either be of the same form or both be linear. By the same form is meant having the same functional dependence on the same number of independent variables with corresponding constants determining a dependent variable.

Preferably, calibration equations for instrument-i and instrument-k have the following linear form:

$$Y_s^i = A^i + \Sigma_j \{B_j^i X_{js}^i\}$$

and $$Y_s^k = A^k + \Sigma_j \{B_j^k X_{js}^k\}$$

where:

$Y_s^i$ is the dependent variable-i in calibration equation-i that preferably assumes a value substantially equal to property-p of any member, s, of said sample-s and $Y_s^k$ is the dependent variable k in calibration equation-k which is functionally related to $Y_s^i$ by a function-f;

$A^k$ and $A^i$ are each intercept or bias constants-i and -k in calibration equations-i and -k, respectively;

$X_{js}^i$ and $X_{js}^j$ are each one of said at least one independent variable-i and -k in calibration equations-i and -k, respectively, having a value equal to at least one said spectral feature-i and -k, respectively of a member, s, at wavelength-j, and;

$B_j^i$ and $B_j^k$ are slope constants-i and -k, respectively, corresponding to coefficients for each said at least one independent variable-i and -k corresponding to spectral features-i and -k at wavelength-j, respectively.

There may be virtually an infinite variety of ways of substituting values for constants-k that yields a calibration equation-k with an SEP not substantially greater than the SEE or SEP necessarily present in the direct method used at some point to obtain directly or indirectly calibration equation-i. By "substantially greater" is meant 30% greater, but preferably, 20% greater, and still more preferably, 10% greater. Directly determined values of property-p must at least once be obtained by some primary or direct test method, in order to calibrate an instrument by determining its calibration equation for predicting values for a physical or chemical property, property-p, for an array of materials, based upon spectral data for such materials. However, once one has calibrated a first instrument, one can use such instrument to calibrate other instruments without necessarily remeasuring property-p by the primary test method. Instrument-i has a directly-determined calibration equation-i if some or all of the constants-i therein are determined by values directly determined by the primary test method. However, where only values used to determine constants-k arise from values predicted by a previously calibrated instrument, without values from the primary test method for property-p, then instrument-k is indirectly calibrated. In all cases, there will be at least one instrument whose calibration equation is determined primarily based upon values for its dependent variable determined by recourse to a primary test method. It is the SEE or SEP of that primary test method which is being referred to above.

However, we have found that the following criteria are particularly useful in determining constants-k assuming that calibration equations-k and -i have a linear form as defined above. One criterion requires that constants-k corresponding respectively to $B_j^k$ and $A^K$ minimize to substantially the maximum degree possible the following expression: $\Sigma_c(Y_c^k - A^k - \Sigma_j B_j^k X_{jc}^k)^2$.

Alternatively, values of $B_j^k$ and $A^k$ can be used which substantially satisfy the following two equations simultaneously: $B_j^k = B_j^i \Sigma_c X_{jc}^i X_{jc}^k / \Sigma_c (X_{jc}^k)^2$ and $A^k = \Sigma_c(Y_c^k - \Sigma_j B_j^k X_{jc}^k)/n$; where n=number of members of sample-c.

Finally, we have also found a particularly useful criteria for determining constants-k corresponding to $B_j^k$ and $A^k$ is one which involves substantially satisfying the following two equations simultaneously: $B_j^k = B_j^i \Sigma_c X_{jc}^i / \Sigma_c (X_{jc}^k)$ and $A^k = \Sigma_c(Y_c^k - \Sigma_j B_j^k X_{jc}^k)/n$.

Step Two involves a slope and bias correction. The requirements for samples appropriate to a slope and bias correction are discussed in the Examples. Essentially, a slope and bias correction arises from determining values for "m" and "b" which satisfy the following expression:

$$m = [(\Sigma_c Y_c^a \Sigma Y_c^k)/n - \Sigma_c(Y_c^a Y_c^k)]/[\{\Sigma_c Y_c^k \Sigma_c Y_c^k\}/n - \Sigma_c Y_c^k Y_c^k]$$

$$b = \{\Sigma_c Y_c^a - m \Sigma_c Y_c^k\}/n$$

where:

$Y_c^a$ is a directly or indirectly determined value for property-p of a particular member, c, of sample-p that is determined with an inferred standard error of estimate no greater than E of the primary test method; and wherein said value for property-p is within the range of interest;

n is the number of members of sample-p; and v is the standard error of estimate from using calibration equation-k values to determine dependent variable-k, for sample member, c, wherein v is not significantly greater than E.

Substitute said values for m and b into the following expression and an improved calibration equation results for the dependent variable-k for instrument-k, which is as follows:

$^*Y_c^k = [mA^k + b] + \Sigma_j[mB_j^k X_{jc}^k]$.

Step Two may in some instances be omitted because the correction suggested or required by applying a slope and bias correction does not result in a significant change in constants-k for calibration equation-k (See FIG. 1, Box G). But it is preferable to carry out the steps involved in a slope and bias correction to determine whether a significant correction is involved or not. We have found in most instances, a slope and bias correction is required.

What is surprising about Step Two, the slope and bias correction, is that even a significant variation in values of constants-k required by or due to the correction does not mean that an error has occurred in carrying out Step One. We have discovered that the error, if any, in Step One is substantially corrected by a slope and bias correction and vice versa. (See Example 1). Further, we have found that the number of samples required to carry out a slope and bias correction, even when added to those required to carry out Step One, are together far fewer in number than was required to determine calibration equation-i for instrument-i. This is totally unexpected and could not have been anticipated. In fact, when a significant correction in constants is indicated by a slope correction, the art (see manual for Near Infrared Spectral Analysis Software published by NIR Systems, Inc. Silver Spring, Md. 1989) teaches that one should recalibrate instrument-k by the same method used to initially calibrate instrument-i.

Closer examination of what is happening to the constants-k in calibration equation-k as one applies Steps One and Two is interesting. In Step One, each constant varies substantially independently in order to satisfy the set of numerical criteria discussed above. In Step Two, slope constants all vary together by an amount determined by "m". Intercept constant-k is impacted in two ways, both by "m" and an incremental amount "b". When applied together, a calibration equation-k for instrument-k preferably provides an SEP for dependent variable-k that is almost as good as, and often much better than that achieved by calibration equation-i using data measured by instrument-i or at least an SEP that is equal to or better than E, the value of SEP for the direct test method for determining values used to calibrate instrument-i. This result shown in the examples, is totally unexpected, surprising and valuable.

Also contemplated by this invention is the indirect method for determining a property-p for a sample-u using spectral data-k measured by an instrument-k, capable of determining such spectral data-k for sample-u. Though the art teaches many ways for identifying a calibration equation for an instrument, the art has not provided up till now an easy method for transforming a calibration equation-i appropriate for instrument-i to a calibration equation-k appropriate for instrument-k.

A unique form for calibration equation-k or -i involves the use of adjacent order differentials as spectral features. For example, the calibration equation for instrument-k and instrument-i each have the form:

$Y_c^k = A^k + \Sigma_j B_j^k X_{jc}^k + \Sigma_{jc} C_j^k X_{jc}^{lk}$ $Y_c^i = A^i + \Sigma_j B_j^i X_{jc}^i + \Sigma_c C_j^i X_{jc}^{li}$.

Here $Y_c^i$, and $Y_c^k$ are calculated or predicted values for dependent variables based upon the calibration equations for instruments-i and -k, respectively, both for each member, c, from sample-c.

$X_{jc}^i$, and $X_{jc}^k$ are second derivatives of observed absorbances for instruments I and k, respectively, both for each member, c, from sample-c at wavelengths-j.

$X_{jc}^{li}$, and $X_{jc}^{lk}$ are the third derivative for observed absorbances for instruments-i and -k, respectively, both for sample-c at wavelength-j.

We have discovered that with calibration equations in the form of adjacent orders of derivatives of spectral data, that surprisingly a slope and bias correction brings about a variation in calibration equation constants-k that results inferred values for property-p of a sample, c, based upon spectral data measured for sample-c by instrument-k that is in excellent agreement with the results found from instrument-i and calibration equation-i.

EXAMPLE 1

A calibration equation for an uncalibrated instrument is obtained based upon the calibration equation established for a reference instrument. Solutions for the following equations determine: $B_j^k$'s and $A^k$ in the linear calibration equation for instrument-k, the uncalibrated instrument, having the form: $Y_c^k = A^k + \Sigma_j B_j^k X_{jc}^k$; which relies on calibration equation: $Y_c^i = A^i + \Sigma_j B_j^i X_{jc}^i$; for a calibrated or reference instrument, instrument-i.

Three different mathematical criterions are used independently. Since only three wavelengths are used, J=1 to 3; and since 25=total number of members in sample-c, c=1 to 25. Independent variables, $X^k_{jc}$, (where "k" identifies instrument-k) have values for spectral features derived from the spectral response of instrument-k at wavelength-j. Each wavelength-j is within the wavelength range of from 800 to 2500 nm. Here the spectral features are the second derivative of the absorbance determined at three wavelengths-J: 1196, 1220, and 1286 nm.

Mathematical Criterion I $\Sigma_c(Y_c^i - A^k - \Sigma_j B_j^k X_{jc}^k) = 0$; Assume $Y_c^i = Y_c^k$ $\Sigma_c Y_c^i X_{1c}^k - A^k \Sigma_c X_{1c}^k - B_1^k \cdot \Sigma_c X_{1c}^k X_{1c}^k - B_2^k \cdot \Sigma_c X_{2c}^k X_{1c}^k - B_3^k \cdot$ $\Sigma_c X_{3c}^k X_{1c}^k = 0$;

$\Sigma_c Y_c^i X_{2c}^k - A^k \Sigma_c X_{2c}^k - B_1^k \cdot \Sigma_c X_{1c}^k X_{2c}^k - B_2^k \cdot \Sigma_c X_{2c}^k X_{2c}^k - B_3^k \cdot$ $\Sigma_c X_{3c}^k X_{2c}^k = 0$;

and $\Sigma_c Y_c^i X_{3c}^k - A^k \Sigma_c X_{3c}^k - B_1^k \cdot \Sigma_c X_{1c}^k X_{3c}^k - B_2^k \cdot \Sigma_c X_{2c}^k X_{3c}^k - B_3^k \cdot$ $\Sigma_c X_{3c}^k X_{3c}^k = 0$ Instrument-i is calibrated using multiple linear regression at the second derivative of absorbance at 1196, 1220, and 1236 nm modeling the dependent variable (R+M)/2 octane using 72 gasoline samples encompassing the octane range of 86-93 in an approximate box car distribution. Instrument-i is a NIR Systems 6500 operating in transflectance mode using fiber optics at a path length of 18 mm.

From the regression equation for instrument-i, one obtains values of 25 calibration transfer standards and subsequently assigns these as values of the dependent variable (R+M)/2 octane for the 25 calibration transfer standards. The standards are the same ones seen in Example 2.

The 25 calibration transfer standards and 10 samples of known octane are run on instrument-k. The results are summarized in Table 1.

Mathematical Criterion II $$B_r^k = [B_r^i \Sigma_c X_{rc}^i X_{rc}^k]/[\Sigma_c (X_{rc}^k)^2]$$

$$A^k = \Sigma_c(Y_c^k - \Sigma_r B_r^k X_{rc}^k)/n \quad \text{Assume } Y_c^i = Y_c^k$$

NOTE:
$r = 1-3$; since only three wavelengths 1196, 1220, and 1236 are used; and $n = 25$; since number of members in sample-c is 25.

Instrument-i is calibrated using multiple linear regression at the second derivative of absorbance at 1196, 1220, and 1236 nm modeling the dependent variable (R+M)/2 octane using 72 gasoline samples encompassing the octane range of 86–93 in an approximate box car distribution. Instrument-i is a NIR Systems 6500 operating in transflectance mode using fiber optics at a path length of 18 mm.

From the regression equation for instrument-i, one obtains values of 25 calibration transfer standards and subsequently assigns these as values of the dependent variable (R+M)/2 octane for the 25 calibration transfer standards. The standards are the same ones seen in Example 2.

The 25 calibration transfer standards are run on instrument-k. Regression constants are calculated as follows:

$$B_1^k = B_{1220}^k = [B_{1220}^i \Sigma X_{1220,c}^i X_{1220,c}^k]/\Sigma(X_{1220,c}^k)^2$$

$$A^k = \Sigma_r[Y_{25}^2 - (B_{1220}^k X_{1220,r}^k) - (B_{1196}^k X_{1196,r}^k) - B_{1236}^k X_{1236,r}^k)]/n.$$

The above constants in the calibration equation predict the value of 10 samples of known octane. There is a severe bias of 5.314 (R+M)/2 octane numbers. A computer program establishes that a slope correction of 0.56741 is needed and an intercept correction of 35.646.

These adjustments yield the final slope and bias adjusted calibration equation for instrument-k and show a standard error of estimate of 0.184 and bias of 0.0265 (R+M)/2 octane numbers on the remaining 62 samples.

Mathematical Criterion III $$B_r^k = B_r^i \Sigma_c X_{jc}^i/\Sigma_c X_{jc}^k$$

$$A^k = \Sigma_c(Y_c^k - \Sigma_r B_r^k X_{rc}^k)/n \quad \text{Assume } Y_c^i = Y_c^k$$

NOTE:
$r = 1-3$; since only three wavelengths are used.
$n = 25$; since number of members in sample-c is 25.
Just as with Criterion II, the above Criterion III are used. The results of all methods are given in Table 1.

To demonstrate the relative accuracy to be expected from an octane calibration equation transferred from one instrument, instrument-i to another, instrument-k, the following is done.

Both instrument-i and instrument-k are each independently calibrated using the same 72 samples. The calibration establishes a linear calibration equation that can be used to predict octanes. A standard error of prediction for each of these equations is established for ten knowns.

The transfer calibration equations for instrument-k is derived from calibration equation-i and one of the following criterion: I, II, or III.

Each transferred equation is slope and bias corrected with ten samples yielding a slope and bias corrected calibration equation.

The results from the above steps are shown in Table 1. What is particularly significant is that the SEP dramatically changes as a result of the slope and bias correction. However, the final SEP, after performing a slope and bias correction, in the case of Criterion I, yields an SEP identical to that of the original calibration equation-i.

A good estimate of the best SEP one might expect in this instance would be an SEP of 0.146 which is the SEP for instrument-k when fully calibrated using the 72 samples.

TABLE 1

| | Calibration Transfer Without Slope & Bias Correction | | | | |
|---|---|---|---|---|---|
| | 10 Samples Transfer Calibration Equation-k Using 25 Standards of Table 1 | | | Original Calibration | Independent Calibration of |
| | Criterion I | Criterion II | Criterion III | Equation-i (72 Samples) | Instrument-k (72 Samples) |
| $A^k$ | 74.501 | 76.041 | 75.560 | 76.263 | 70.918 |
| $B_1^k$(1220 nm) | 134.620 | 206.02 | 211.90 | 124.60 | 131.21 |
| $B_2^k$(1196 nm) | 21.139 | 26.939 | 26.940 | 24.407 | 13.48 |
| $B_3^k$(1236 nm) | 69.345 | 70.681 | 70.689 | 65.546 | 65.251 |
| SEP | 0.366 | 5.383 | 5.523 | 0.156 | 0.146 |
| Bias | −0.288 | 5.195 | 5.314 | 0 | 0 |

| | Calibration Transfer With Slope & Bias Correction | | | |
|---|---|---|---|---|
| | 62 Samples Transfer Calibration Equation-k Using 25 Standards of Table 1 | | | Independent Calibration of |
| | Criterion I | Criterion II | Criterion III | Instrument-k (72 Samples) |
| $A^k$ | 76.013 | 78.792 | 78.753 | 70.918 |
| $B_1^k$(1220 nm) | 123.20 | 116.90 | 116.86 | 131.21 |
| $B_2^k$(1196 nm) | 19.345 | 15.285 | 14.857 | 13.48 |
| $B_3^k$(1236 nm) | 63.460 | 40.105 | 38.985 | 65.251 |
| SEP | 0.156 | 0.184 | 0.188 | 0.146 |

TABLE 1-continued

| | | | | |
|---|---|---|---|---|
| Slope Adjustment (m) | 0.91514 | .56741 | 0.55150 | 1 |
| Bias Adjustment (b) | 7.8341 | 35.646 | 37.082 | 0 |
| Bias | 0.0191 | 0.0265 | 0.0373 | 0 |

EXAMPLE 2

In this example, Mathematical Criterion I of Example 1 (multiple linear regression) is used and the form of the calibration equation is linear, but spectral features equal to second and third adjacent derivatives of spectral data corresponding to each selected frequency are used for the independent variables.

$$Y_c^k = A^k + \Sigma_j B_j^k X_{jc}^k + \Sigma_{jc} C_j^k X_{jc}^{lk}$$

$$Y_c^i = A^i + \Sigma_j B_j^i X_{jc}^i + \Sigma_c C_j^i X_{jc}^{li}$$

Here $Y_c^i$, and $Y_c^k$ are calculated or predicted values for dependent variables based upon the calibration equations for instruments-i and -k, respectively, both for each member, c, from sample-c having 8 members.

$X_{jc}^i$, and $X_{jc}^k$ are second derivatives of observed absorbances for instruments i and k, respectively, both for each member, c, from sample-c at wavelength-j, where j=1 to 3.

$X_{jc}^{li}$, and $X_{jc}^{lk}$ are the third derivative for observed absorbances for instruments-i and -k, respectively, both for sample-c at wavelength-j, where j=1 to 3.

The three wavelengths are the same as used in Example 1.

Seventy-two gasoline samples are analyzed on instrument-i to obtain their absorbance spectra. In addition, 25 samples of calibration transfer standards are also run. The second and third derivatives of the spectra are then made using segment lengths of 20 and gaps of 0 on NSAS (Near Infrared Spectral Analysis Software, available from NIR Systems, Inc.). The compositions of the 25 calibration transfer standards are shown in Table 7, and are specifically chosen because they encompassed the majority of variance of the 72 gasoline samples at the wavelengths used in the calibration. The 72 gasoline samples have octane in the range of 86.3–93.2 (R+M)/2 octane numbers and are distributed among this range in an approximate box car distribution. Each sample is analyzed four times by four different knock engine laboratories (APAL, No. 2 Control Lab, Canton Control Lab, and St. Paul Control Lab) by ASTM methods 2699 and 2700 to provide accurate estimates of (R+M)/2 octane.

The second and third derivative files of the 72 gasoline samples are sent to a mainframe computer, and a multiple linear regression in accordance with Mathematical Criterion I is performed by conventional computer programs using SAS statistics (available from SAS Institute, Inc., Cary, N.C. on the second derivative of absorbance at 1196, 1220, and 1236 nm and the third derivative of absorbance at 1196, 1220, and 1236 nm modeling the dependent variable of (R+M)/2 octane. Analysis of the data in this way provides a multiple linear regression model of the form:

$$Y_c^i = [(R+M)/2]\text{octane} = A^i + B_1^i(X_{1c}^i) + B_2^i(X_{2c}^i) + B_3^i(X_{3c}^i) + C_1^i(X_{1c}^{li}) + C_2^i(X_{2c}^{li}) + C_3^i(X_{3c}^{li}).$$

The values of the $B_i$ terms are shown in Table 2. The multiple coefficient of determination ($R^2$), multiple coefficient of correlation (R), F-value and standard error of estimate are shown in Table 2. It can be concluded from Table 2 that the calibration equation is extremely accurate.

TABLE 2

Regression Constants Obtained for the Calibration Equation-i of the 72 Gasoline Samples

| Variable | Wavelength | Derivative Used | Value |
|---|---|---|---|
| $A^i$ | Constant | — | 71.18951 |
| $B_1^i$ | 1220 nm | 2nd | 46.25463 |
| $B_2^i$ | 1196 nm | 2nd | −22.35057 |
| $B_3^i$ | 1236 nm | 2nd | 64.61244 |
| $C_1^i$ | 1220 nm | 3rd | −28.34514 |
| $C_2^i$ | 1196 nm | 3rd | −12.83303 |
| $C_3^i$ | 1236 nm | 3rd | −66.41106 |

Statistical Results For the Calibration Equation-i

| Multiple Coefficient of Determination | Multiple Coefficient of Correlation | F-Value | Standard Error of Estimate |
|---|---|---|---|
| 0.9962 | 0.9980 | 2805 | 0.145 |

Next the values of the Calibration Transfer Standards are predicted from the calibration equation of instrument-i and the predicted values are used as the dependent variable ((R+M/2) octane) and the absorbance data for the Calibration Transfer Standards on instrument-k are converted to second derivative and third derivative and are used for the values of the independent variables-k to determine relevant constants-k using the classical least squares method or Mathematical Criterion I. The results are given in Table 3.

TABLE 3

Regression Constants Obtained on Instrument-k For the 25 Calibration Transfer Standards

| Variable | Wavelength | Derivative Used | Value |
|---|---|---|---|
| $A^k$ | Intercept | — | 55.55131 |
| $B_1^k$ | 1220 | 2nd | 179.49118 |
| $B_2^k$ | 1196 | 2nd | −47.22965 |
| $B_3^k$ | 1236 | 2nd | 130.60840 |
| $C_1^k$ | 1220 | 3rd | −71.70553 |
| $C_2^k$ | 1196 | 3rd | −50.71056 |
| $C_3^k$ | 1236 | 3rd | 18.43823 |

Table 4 shows the statistical data for calibration equation-k.

TABLE 4

Statistical Data for the Calibration Transfer to Instrument-K Using the Octanes Predicted from Instrument-I

| Multiple Coefficient of Determination | Multiple Coefficient of Correlation | F-Value | Standard Error of Estimate |
|---|---|---|---|
| 0.9988 | 0.9994 | 2544 | 0.124 |

Seventy-two gasoline samples were then run on instrument-k and second and third derivative files are obtained as before. The new calibration equation from Table 3 is used to predict the (R+M)/2 octane of the 72 gasoline samples using the same octane as is used in the original calibration of instrument-i. These calculations are done on a PC using a BASIC program. The calculated octanes show a bias of −0.431 and have a standard error of prediction of 0.586. These errors are quite high considering that the original standard error of estimate on instrument-i is only 0.145. Also, it could be seen from the predicted octanes that the error for low octane predictions ((R+M)/2 approximately equal to 86) is quite high (i.e., about −0.8) when compared to the higher octane ((R+M)/2 approximately equal to 93) predictions (e.g., much closer to zero, about 0.1). This type of behavior is similar to heteroscedasticity, in that calculated predictions tend to be erroneous by an amount that is a function of estimated octane. For example, lower octanes yielded high errors and higher octanes yielded lower errors. When the above behavior is observed, a slope and bias adjustment is warranted providing that a plot of (Y actual-Y predicted) versus octane approximates a straight line. This ordinarily is the case providing that the original calibration equation is linear or a non-linear equation transformed so as to obtain a linear relationship. From examining the data, it is clear that a slope adjustment is warranted since the relationship approximates a straight line. A PC BASIC program is used to accomplish this and shows that a slope correction for "m" of 0.86406, and a bias correction for "b" of 12.5590 is needed.

$$Y(\text{Predicted}) = Y_c^k = [0.86406(A^k + \Sigma_{i=1}^{72} B_i^k X_{ic}^k + \Sigma_{i=1}^{72} C_i^k X_{ic}^{lk})] + 12.5590.$$

Table 5 shows the final regression constants for instrument-k using the calibration transfer followed by the slope and bias correction.

This equation is found to have a standard error of estimate of 0.190 on instrument-k compared to instrument-i's standard error of 0.145 on the 72 gasoline samples.

TABLE 5

Final Regression Constants for the Slope and Bias Corrected Transferred Calibration for Instrument-i

| Variable | Wavelength | Derivative Used | Value |
|---|---|---|---|
| $A^i$ | Intercept | — | 60.55866 |
| $B_1^i$ | 1220 | 2nd | 154.22709 |
| $B_2^i$ | 1196 | 2nd | −40.80925 |
| $B_3^i$ | 1236 | 2nd | 112.85349 |
| $C_1^i$ | 1220 | 3rd | −61.95788 |
| $C_1^i$ | 1196 | 3rd | −43.81697 |
| $C_1^i$ | 1236 | 3rd | 15.93174 |

EXAMPLE 3

This example demonstrates the slope and bias correction referred to earlier in this specification (Analytica Chemica Acta, 192(1987),197).

The various terms are as previously defined throughout this specification, the Y-term is a dependent variable calculated or predicted based upon independent variables equal to one or more spectral features identified as X-terms.

Depending upon the size or magnitude of the slope and bias corrections corresponding to m and b; where m is the slope correction and b is the bias correction, one may decide not to modify the calibration equation for the uncalibrated instrument. $\hat{Y}_c^k$ is the slope-corrected and bias-corrected value predicted for a physical property as shown hereinafter.

In the specific example $Y_c^k$, the predicted octane value from calibration equation-k, before the slope and bias correction, and $Y_c^k$, the sample measured octane (or octane predicted by a calibrated NIR instrument), are used to determine the slope and bias corrections. In the sample set that is used to do a slope and bias correction, it is necessary that the set:

1. Be representative of the range of interest for a particular property, for example, octane. The sample then should have actual octane values (measured in accordance with ASTM D2699 and D2700) approximately in the range of octane values of interest.
2. Have the octane measured for each sample, and that this actual octane value be then correlated (in effect plotted) versus the calculated octane value for each sample determined by using the calibration equation to which the slope and bias correction is to be made.
3. The number, n, of samples used for making the slope and bias correction must be 2 to define both m and b, but in the examples, 10 is usually used. $Y_c^k = A^k + \Sigma_c B_j^k X_{jc}^k$ The calibration equation for instrument-k $Y_c^a$ is the directly determined, or actually measured property; here ASTM measured octane.
4. To find m and b, solve for m and b which satisfy the following mathematical criteria:

$$\Sigma_c (Y_c^k Y_c^a)^2 - m \Sigma_c Y_c^k Y_c^k - b \Sigma Y_c^k = 0$$

$$\Sigma_c (Y_c^a - m Y_c^k - b) = 0.$$

The results are:

$$m = [(\Sigma_c Y_c^a \Sigma Y_c^k)/n - \Sigma_c (Y_c^a Y_c^k)] / [\{\Sigma_c Y_c^k \Sigma_c Y_c^k\}/n - \Sigma_c Y_c^k Y_c^k]$$

$$b = 1/n \{\Sigma_c Y_c^a - m \Sigma_c Y_c^k\}$$

$$\hat{Y}_c^k = [mA^k + b] + \Sigma_j (mB_j^k X_{jc}^k).$$

EXAMPLE 4

The mathematical treatment is changed from Multiple Linear Regression to Partial Least Squares for calibration transfer to instrument-k from instrument-i.

In this example, instrument-i is a NIR Systems 6500 bench top instrument operating in transflectance mode using fiber optics. The instrument is calibrated as shown in Example 1 using the 72 gasoline samples. The calibration is made as before modeling (R+M)/2 octane using the second derivative of absorbance at 1220, 1196 and 1236 nm as independent variables for the multiple regression calibration equation. The calibration transfer standards are the same 25 as shown in Example 5.

Instrument-k is an uncalibrated NIR Systems OL-6500 operating in transflectance mode using fiber optics. The 25 calibration transfer standards are run on this instrument using the calculated octanes, from instrument-i, as the dependent variable. This invention makes it possible to calibrate instrument-k using a different mathematical approach from that which is used on instrument-i (multiple linear regression). Partial Least Squares (PLS) is chosen as the alternative calibration method for instrument-k. The principles of PLS are well known (Harold Martens and Tormod Naes, Multivariate Calibration, John Wiley & Sons; New York, 1989 [ISBN 471-90979-3]).

PLS is accomplished by modeling the dependent variable of calculated octane for the 25 calibration standards second derivatives of absorbance over the wavelength range of 1190–1240 nm (in 2 nm intervals, i.e., 1190, 1192, 1194 . . . 1240). Cross validation is accomplished using four subset groups. Models are developed using one, two, three, four, five, and six latent variables. The four latent variable model seems to provide the best estimate of pump octane for instrument-k (i.e., accounted for the most variance without overfitting the data), and a correlation of 0.9994 with instrument-i's calculated octane values. The four latent variable PLS model is used to predict the values of the first 10 samples of the original 72 sample calibration set. The predicted values show a substantial bias of −0.433 (R+M)/2 octane numbers, and a standard error of 0.468. A slope adjustment of 0.940 and an intercept adjustment of 5.77 (R+M)/2 octane numbers is made. The remaining 62 samples are predicted as unknowns. The 62 samples show a bias of 0.0156 octane numbers and a standard error of prediction of 0.153 octane numbers for the unknowns.

It should be noted that a different area of the spectra other than 1190–1240 can be chosen, provided that it is functionally related to octane with a reliability at least as good as that for measuring such octane directly.

EXAMPLE 5

Figure 2:
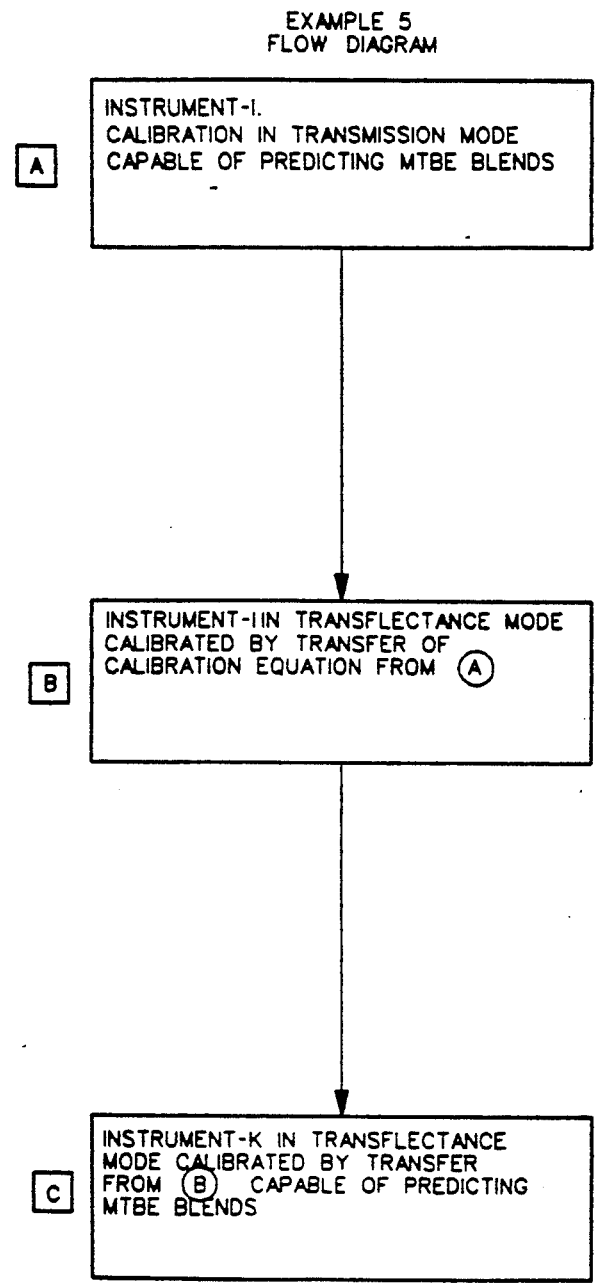
FIG. 2 is a flow diagram for Example 5.

This example discloses transferring a calibration equation suitable for MTBE from one refinery to another without MTBE from one knock engine to another, from one instrument after a configuration and lamp change to another instrument, with a substantially decreased error of prediction, by means of a double calibration transfer (See FIG. 2).

This example dramatically demonstrates a utility of the present invention. For example, instrument-k is fully calibrated using only gasolines which contained no MTBE (methyl t-butyl ether) (See FIG. 2, Box A). Recently, Congress passed the reformulated fuels act and since instrument-k operates in a refinery that is in a CO (carbon monoxide) non-attainment area, the reformulated fuels act specifies that this refinery must begin adding MTBE (or some other oxygenated feedstock) to its gasoline blends at some future date. Because instrument-k is calibrated without the use of MTBE, it is expected that substantial errors would result if instrument-k's current calibration is used on unknown samples which contain MTBE. To keep from completely recalibrating instrument-k, one would want to transfer a calibration equation which can accommodate MTBE as it is added to the refineries gasoline blending stocks at a future date. In this example, instrument-k is a NIR Systems OL-6500 operating in transflectance mode using fiber optics (See FIG. 2, Box B).

A NIR Systems 6500 is chosen to operate as instrument-i because it was once calibrated using 226 samples, some of which contained MTBE, and can accommodate samples containing 0–15% by volume MTBE (See FIG. 2, Box A).

The problem is somewhat compounded by the fact that the only calibration standards run on instrument-i during its calibration with MTBE were the eight pure compounds (and calculated octanes) shown in Table 6. These eight compounds are not run on instrument-k, so a direct calibration transfer is not possible.

TABLE 6

| | |
|---|---|
| Isooctane | 98.59200 |
| n-decane | 42.46400 |
| 1-octene | 57.33100 |
| 2,3,4-trimethylpentane | 100.37100 |
| n-heptane | 58.10600 |
| Cyclohexane | 32.51100 |
| n-hexane | 66.06500 |
| Toluene | 101.69200 |

To accomplish the transfer, the eight calibration standards (Table 6) are run on instrument-i again. Since the calibration of instrument-i for the MTBE calibration, instrument-i has been changed from transmission measurements at a path length of 20 mm to transflectance measurements at a path length of 18 mm using fiber optics (See FIG. 2, Box B). The lamp and detector gain are changed as well.

Under the new set of conditions, using the eight calibration standards, the calibration for MTBE is transferred from instrument-i in transmission to instrument-i in transflectance (See FIG. 2, Box B). This equation, without slope and bias or other methods of error correction (e.g., least squares) is then used to calculate predicted octanes for the 25 calibration standards which are also run on instrument-i in transflectance and instrument-k in transflectance (See FIG. 2, Box C).

Multiple linear regression on the 25 calibration standards on Table 7 on instrument-k using the calculated octane values as dependent variables and the second derivative of absorbance at 1220, 1196, and 1236 nm, yielded instrument-k's new calibration equation which could be used to predict the octanes of gasoline blends containing MTBE.

TABLE 7

| | Composition of Calibration Transfer Standards | | | | | | | | |
|---|---|---|---|---|---|---|---|---|---|
| | Paraffins | | Isoparaffins | | Aromatics | | | Naphthenes | Olefins |
| Sam. | Hexane | Heptane | 2,3-Dimethyl Butane | Isooctane | Ethylbenzene | S-Butylbenzene | T-Butylbenzene | *1,2-Dimethyl Cyclohexane | * 1-Octene |
| 1 | 10% | | 35% | | | 40% | | 5% | 10% |
| 2 | 15% | | 35% | | | 40% | | 5% | 5% |
| 3 | 10% | | 40% | | | 40% | | 5% | 5% |
| 4 | 10% | | 35% | | 40% | | | 5% | 10% |
| 5 | 10% | | 35% | | 40% | | | 10% | 5% |
| 6 | 15% | | | 30% | | | 40% | 10% | 5% |
| 7 | 10% | | | 40% | | | 30% | 5% | 15% |
| 8 | 15% | | | 35% | | | 35% | 10% | 5% |
| 9 | 10% | | | 45% | | | 30% | | 15% |
| 10 | 15% | | 30% | | | | 35% | 10% | 10% |
| 11 | 10% | | 40% | | | 40% | | | 10% |
| 12 | | 15% | | 40% | | | 30% | 5% | 10% |
| 13 | 10% | | 5% | 45% | | | 25% | 5% | 10% |
| 14 | | 10% | 35% | | 40% | | | 5% | 10% |
| 15 | | 15% | | 35% | | | 35% | 10% | 5% |
| 16 | 5% | | 40% | | | 40% | | 10% | 5% |
| 17 | 10% | | 40% | | | 45% | | 5% | |
| 18 | 10% | | 20% | 20% | | 20% | 20% | 5% | 5% |
| 19 | 5% | | | 45% | | 40% | | 5% | 5% |

TABLE 7-continued

Composition of Calibration Transfer Standards

| | Paraffins | | Isoparaffins | | Aromatics | | | Naphthenes | Olefins |
|---|---|---|---|---|---|---|---|---|---|
| Sam. | Hexane | Heptane | 2,3-Dimethyl Butane | Isooctane | Ethylbenzene | S-Butylbenzene | T-Butylbenzene | *1,2-Dimethyl Cyclohexane | * 1-Octene |
| 20 | 5% | | 45% | | | 40% | | 5% | 5% |
| 21 | 10% | | | 50% | | | 25% | 5% | 10% |
| 22 | 15% | | | 50% | | | 25% | 5% | 5% |
| 23 | 10% | | 5% | 50% | | | 20% | 5% | 10% |
| 24 | 15% | | 2,3,4-Trimethyl Pentane 30% | 10% | | 15% | 15% | 5% | 10% |
| 25 | 20% | | 2,3,4-Trimethyl Pentane 30% | 5% | | 10% | 25% | 5% | 5% |

*Note
1,2-dimethyl cyclohexane and 1-octene are each a mixture of cis and trans isomers.

The new equation is slope and bias adjusted on ten gasoline samples. Four of these samples are premium unleaded gasoline blends [(R+M)/2 octane≈92] and the remaining six are regular unleaded gasoline blends [(R+M)/2≈87]. These samples show a bias of −0.919 and a standard error of 0.946 (R+M)/2 octane numbers.

From this data, a slope correction of 0.950 and a bias correction of 5.30 is made. The resulting equation shows a bias of 0.0401 and a standard error of prediction of 0.122 on 30 unknown gasoline samples. Some of the pertinent data is summarized below.

SUMMARY TABLE

| Parameter | Original Calibration on instrument-i in transmission | Equation on instrument-i for 8 calibration transfer standards in transflectance | Equation on instrument-k for 25 calibration transfer standards in transflectance | Final calibration equation on instrument-k after slope and bias correction |
|---|---|---|---|---|
| A | 87.925 | 87.318 | 86.238 | 87.226 |
| $B_1$ (1220) | 69.864 | 94.418 | 102.601 | 97.471 |
| $B_2$ (1196) | 18.581 | 23.340 | 22.488 | 21.364 |
| $B_3$ (1236) | 27.644 | 28.058 | 29.838 | 28.346 |
| Correlation with (R + M)/2 octane | 0.992 | * | 0.997 | 0.998 |
| Standard Error of Prediction | 0.330 | * | 0.946 | 0.122 |
| Bias | 0 | * | −0.919 | 0.0401 |

The Summary Table shows a very interesting phenomenon in that the transferred calibration equation is approximately two times more accurate than the original equation. This would appear to stem solely from the fact that the octanes used in the slope and bias adjustment for instrument-k are more precisely known than the calibration samples used on instrument-i.

This example also goes against a commonly held opinion of some NIR spectroscopists. These scientists believe that an equation developed for one refinery is not useful for predictions at another. In this example, the MTBE calibration for instrument-i is developed at Ashland's Catlettsburg refinery. Catlettsburg is a very complex refinery by industry standards and has 12 gasoline blending components. Instrument-k, on the other hand, analyzes data at Ashland's St. Paul Park, Minn., refinery which has only six gasoline blending components and is relatively much less complex. Moreover, the Catlettsburg and St. Paul Park refineries have almost no overlap in terms of crude slates.

A schematic flow diagram for this example is shown in FIG. 2.

EXAMPLE 6

Figure 3:
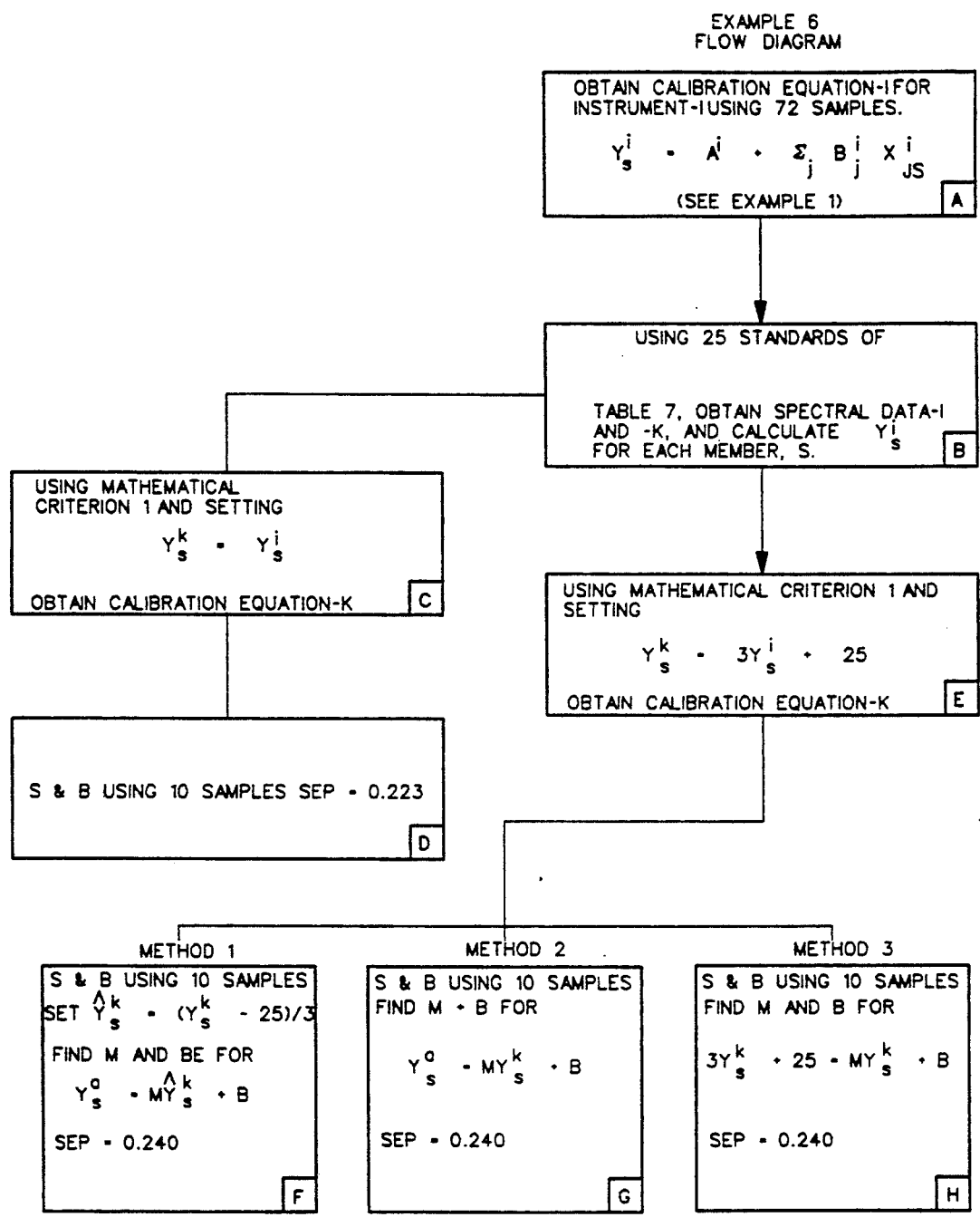
FIG. 3 is a flow diagram for Example 6.

This example, schematically outlined in FIG. 3, demonstrates that when $Y_{k,s}$ is a linear function of $Y_{i,s}$ that the calibration transferred equation is as effective, or approximately as effective, as the equation resulting from the direct calibration transfer of the previous examples; (i.e., where $Y_{i,s(predicted)} = Y_{k,s(actual)}$). Here we will consider the linear function of $Y_{i,s}$ where $Y_{k,s} = -3(Y_{i,s})_{predicted} + 25$ (See FIG. 3, Box E).

In a previous example, an (R+M)/2 octane calibration is shown using 226 samples and predicts the (R+M)/2 octanes of 8 calibration standards (isooctane, n-decane, 1-octene, 2,3,4-trimethylpentane, n-heptane, cychohexane, n-hexane and toluene). This calibration is developed on an NIR Systems Model 6500 operating in transmission mode at a path length of 20 mm (See FIG. 3, Box A).

Subsequently this instrument was configured for fiber optics using transflectance at a path length of 18 mm after the lamp and detector gain setting are changed. The 8 calibration standards are run on the instrument using three times the octane value determined from the transmission measurements plus 25 as the value of the dependent variable (See FIG. 3, Boxes B and E). The results of multiple linear regression are:

$A_k = 286.951$
$B_{k,1220} = 283.252$
$B_{k,1196} = 70.020$
$B_{k,1236} = 84.185$.

Values are then predicted for ten gasoline samples.

The values of the ten gasoline samples predicted are corrected by three-equivalent methods (See FIG. 3, Boxes F, G, and H). Method one (See FIG. 3, Box F)

involves subtracting 25 from the value predicted for the (R+M)/2 gasoline samples, dividing the result by 3, and performing a slope and bias adjustment. Method 2 (See FIG. 3, Box G) involves a slope and bias adjustment using the actually measured octane of the sample. Method three (See FIG. 3, Box H) involves using three times the gasoline samples octane plus 25 for the samples used in the slope and bias adjustment and correcting the values predicted for subsequent unknowns by subtracting 25 and dividing by 3. In each of these three methods, a bias of 0.0281 and a standard error of prediction of 0.240 (R+M)/2 octane numbers is observed using an unknown set consisting of 62 unknowns.

It should be noted that the final equation for the direct calibration transfer ($Y_{i,s\ predicted} = Y_{k,s\ actual}$) (See FIG. 3, in Boxes C and D) shows a somewhat lower error and bias than by either of the previous methods (bias=0.0237, SEP=0.223 (R+M)/2 octane numbers). $Y_{k,s\ actual}$ multiplied by a constant with some other constant added to it yielded a value for the dependent variable for the transfer that had an effect on the error term ($Y_{k,s\ predicted} - Y_{i,s\ actual}$) which is not removed exactly by either the inverse mathematical function or slope and bias adjustment.

However, if we generate the calibration transfer equation (without slope and bias adjustment) and multiply the regression constants ($A_k$, $B_{k,1220}$, $B_{k,1196}$, and $B_{k,1236}$) by three and add 25 to $A_k$, we can arrive at the exact answer that the direct method ($Y_{k,s\ predicted} = Y_{i,s\ actual}$) yields after using a slope and bias adjustment using the actual (R+M)/2 octanes of the ten samples or by slope and bias adjusting the equation using three times the value of octane plus 25 and subtracting 25 from each predicted octane and dividing by 3.

EXAMPLE 7

A calibration equation for an uncalibrated instrument is obtained based upon the calibration equation established for a reference instrument. Solutions for the following equations determine: $B_j^k$'s and $A^k$ in the linear calibration equation for instrument-k, the uncalibrated instrument, having the form: $Y_c^k = A^k + \Sigma_j B_j^k X_{jc}^k$; and which relies on or has recourse to the calibration equation: $Y_c^i = A^i + \Sigma_j B_j^i X_{jc}^i$; for the calibrated or reference instrument, instrument-i.

Mathematical Criterion I, a classical least squares is used. But, since only three wavelengths are used, J=1 to 3; and since 4= total number of members in sample-c, c=1 to 4. Independent variables, $X^k_{jc}$, (where "k" identifies instrument-k) have values for spectral features derived from the spectral response of instrument-k at wavelength-j. Each wavelength-j is within the wavelength range of from 800 to 2500 nm. Here the spectral features are the second derivative of the absorbance determined at three wavelengths-J: 1196, 1220, and 1286 nm.

Mathematical Criterion I $\Sigma_c(Y_c^i - A^k - \Sigma_j B_j^k X_{jc}^k) = 0$;  Assume $Y_c^i = Y_c^k$ $\Sigma_c Y_c^i X_{1c}^k - A^k \Sigma_c X_{1c}^k - B_1^k \cdot \Sigma_c X_{1c}^k X_{1c}^k - B_2^k \cdot \Sigma_c X_{2c}^k X_{1c}^k - B_3^k \cdot$ $\Sigma_c X_{3c}^k X_{1c}^k = 0;$ $\Sigma_c Y_c^i X_{2c}^k - A^k \Sigma_c X_{2c}^k - B_1^k \cdot \Sigma_c X_{1c}^k X_{2c}^k - B_2^k \cdot \Sigma_c X_{2c}^k X_{2c}^k - B_3^k \cdot$ $\Sigma_c X_{3c}^k X_{2c}^k = 0;$ -continued
Mathematical Criterion I and $\Sigma_c Y_c^i X_{3c}^k - A^k \Sigma_c X_{3c}^k - B_1^k \cdot \Sigma_c X_{1c}^k X_{3c}^k - B_2^k \cdot \Sigma_c X_{2c}^k X_{3c}^k - B_3^k \cdot$ $\Sigma_c X_{3c}^k X_{3c}^k = 0$ Note in Mathematical Criterion I, the form of the calibration equation for the reference instrument-i need not be the same as that for the uncalibrated instrument-k.

Even after both changing a bulb which would ordinarily change the spectral characteristics of an instrument, and also reconfiguring the instrument for fiber optics operating in transflectance mode at a different path length, it was possible to recalibrate such instrument by means of the steps of this invention.

A calibration is developed on instrument-i for pump octane. The calibration set consists of 226 samples. These samples are analyzed on instrument-i and a multiple linear regression is performed modeling (R+M)/2 octane at the second derivative of absorbance at 1220, 1196, and 1236 nm. Instrument-i is operating in transmission mode using a total path length of 20 mm. The regression constants obtained are:

$A^i = 87.925$
$B_1^i = 69.864$
$B_2^i = 18.581$
$B_3^i = 27.644$

The standard error of estimate for the equation is 0.330. It should be pointed out that these results are from two different knock engine operators running samples on the same knock engines. These results are considered to be good since the ASTM allowable limits for (R+M)/2 are a standard error of estimate of approximately 0.35. These samples were in an approximate box-car distribution from 84–94 (R+M)/2 octane.

Based on the multiple regression calibration equation values are predicted for four calibration transfer standards. These standards and their calculated (R+M)/2 octanes are shown below.

| Substance | Calculated Octane |
| --- | --- |
| Isooctane | 98.592 |
| n-decane | 42.464 |
| l-octene | 57.331 |
| 2,3,4-trimethylpentane | 100.371 |

It should also be pointed out that instrument-i is calibrated over a four-month period (i.e., samples were run as they came into the lab) and this is not an optimal way to do a calibration. Also not optimal was the fact that these calibration standards were not run on the instrument promptly after or substantially at the same time as the initial calibration, but not until more than one month after the calibration was completed.

Subsequent to this, the lamp on instrument-i burns out and a new lamp is inserted. The instrument is also configured for fiber optics operating in transflectance mode at a different total path length ($\approx$ 18 mm). In addition to the configuration mode and path length changes, the detector gain has to be changed to accommodate the new lamp and lower throughput of the fiber optic configuration (as opposed to transmission).

The calibration transfer standards are rerun on instrument-i and a transferred calibration equation is developed modeling calculated octane as a function of the second derivative of absorbance at 1220, 1196, and 1236 nm.

The regression constants obtained were:

$A^k = 87.717$
$B_1^k = 92.471$
$B_2^k = 24.079$
$B_3^k = 32.054$.

$B_1^k$ is very different from $B_1^i$ whereas $A^k$, $B_2^k$ and $B_3^k$ are within 6 (R+M)/2 octane numbers from $A^i$, $B_2^i$ and $B_3^i$, respectively.

Subsequently, 97 samples are analyzed for (R+M)/2 octane. None of these samples are the same as before. Furthermore they are analyzed by multiple operators on different knock engines from those used before. The calibration transfer equation yields a slight bias of 0.0392 (R+M)/2 octane numbers (note that the bias between two different knock engines is commonly much higher than this) and a standard error of estimate of 0.371 (R+M)/2 octane numbers. A slope and bias adjustment is made using two samples; one at 87.4 octane and one at 92.5 octane, and yields a slope correction of 0.9402 and intercept correction or bias correction of 5.297 and a final equation of:

$A^k = 87.774$
$B_1^k = 86.945$
$B_2^k = 22.640$
$B_3^k = 30.139$.

The slope and bias adjusted equation has a bias of 0.0 and a standard error of prediction of 0.343.

To demonstrate that this could not be accomplished directly from the original calibration equation from transmission data, the original calibration equation is used to predict the (R+M)/2 octane for each of the 97 gasoline samples. The result shows a bias of −0.482 octane. A slope and bias adjustment only using all 97 samples on this original calibration equation shows a bias of 0 and a standard error of estimate of 1.96 (R+M)/2 octane.

MODIFICATIONS

Specific compositions, methods or embodiments discussed are intended to be only illustrative of the invention disclosed by this specification. Variations of these compositions, methods or embodiments are readily apparent to a person of skill in the art based upon the teachings of this specification and are therefore intended to be included as part of the invention disclosed herein.

For example, an equivalent method to those disclosed in the examples, intended to be within the claimed scope of this invention, is determining the bias value for, for example, $A^k$ in calibration equation-k for instrument-k based upon calibration equation-i for instrument-i, wherein the value for $A^i$ is assumed to be equal to some arbitrary value, such as zero, or a value determined in connection with $A^i$ and a function of $A^i$; i.e., a partially calibrated instrument. The "correct" value for $A^k$, is that value which when used in a calibration equation-k determines the value for a dependent variable-k, which is substantially equal to the actual value of a physical or chemical property desired. The "correct" value for $A^k$ can be obtained from employing a slope and bias correction to that equation which resulted from employing an arbitrary value for $A^i$ or a value determined by some function of $A^i$. Another equivalent method like above occurs when the final equation that would otherwise result from a slope and bias equation may be disguised by using a function of either m or b, (the terms discussed in Example 6). This will clearly change the calculated or predicted value for the dependent variable. However, just as was shown in the specification that a function of $Y^i$s from calibration equation-i can be used, so also can a function of m or b be used and then the resulting dependent variable transformed back to a value that will be substantially equal to the actual value for a chemical or physical property of interest.

Still another variation within the scope of this invention involves how values are assigned to dependent variable-k. These values for dependent variable-k, that can be used to determine constants-k in calibration equation-k or for performing a slope and bias correction, can be determined without using a primary test method but instead by reference to calibration equation-i and spectral data-i obtained from instrument-i or possibly any other calibrated instrument in conjunction with its corresponding calibration equation which involves substantially the same range of interest and relevant spectral data.

Still another variation of this invention is to use different spectral features in calibration equation-i from those in calibration equation-k, e.g., different wavelengths or different mathematical transforms or both; provided such differences are each correlatable to a physical or chemical property of interest.

Reference to documents made in the specification is intended to result in such patents or literature being expressly incorporated herein by reference, including any patents or other literature references cited within such documents.

In most examples, only three wavelengths were used. The number, however, can vary depending upon the statistical reliability sought or required. If the indirect method has an SEP of "v" for some property which is smaller than the interval of reliability for the direct method for determining such property, then there is a practical limit to how small it is reasonable to seek to make "v", and how many wavelengths should be required.

Another modification relates to the spectral features which can be derived from absorption spectra. In the examples, both second and higher derivatives of intensities versus wavelengths or absorbances, were used. Clearly, higher derivatives such as first, second, third, fourth, and fifth or higher are also expressly contemplated for this invention. Values for a spectral feature can equal simply the value found for a particular wavelength, or a range of wavelengths around some reference wavelength; e.g., absorbances. Spectral features are not intended to suggest that the spectral data is necessarily different in value from a spectral feature. It is clearly contemplated that it may be more complicated in that a linear combination of spectral features or mathematical transforms thereof are within the intended scope of this invention.

Also contemplated as a variation of this invention is a linear combination of still higher adjacent order derivatives, such as third and fourth order derivatives or higher adjacent order derivatives, of spectral data. See Example 5 for an example.

Further, any set of members or range of numbers cited in the specification is intended to incorporate expressly herein any member or number falling within such set or range, respectively, including any subset or range within any set or range cited.

What is claimed is:

1. In an indirect method for determining a property-p for a sample-u, using spectral data-k measured by an instrument-k, capable of determining such spectral data-k for said sample-u, in combination with a calibration equation-k, having: at least one constant-k; a dependent variable-k; and at least one independent variable-k; wherein each value for said dependent variable-k is determined specifically by specific values for each said at least one independent variable-k, and wherein each said at least one independent variable-k has a value-k equal to a spectral feature-k, functionally determined from said spectral data-k; wherein the improvement comprises:

(1) defining said calibration equation-k by recourse to a calibration equation-i for instrument-i, wherein said calibration equation-i has: at least one constant-i; at least one independent variable-i; and a dependent variable-i; wherein each value for said dependent variable-i is determined specifically by specific values for each said at least one independent variable-i, and wherein each said at least one independent variable-i has a value-i equal to a spectral feature-i, functionally determined from spectral data-i, and wherein calibration equation-i and -k determine, respectively, values for each said dependent variable-k and-i, that are functionally related to one another by a function-f that transforms dependent variable-i into dependent variable-k, said method for defining said calibration equation-k by recourse to said calibration equation-i comprising:

(a) obtaining respectively with instrument-i and instrument-k spectral data-i and spectral data-k, respectively, for each member of a sample-c, comprising at least one member c, thereby functionally determining value-k and value-i, respectively, equal to said at least one spectral feature-k and said at least one spectral feature-i, respectively, for each member of sample-c used in step (b);

(b) determining, in accordance with calibration equation-i, a value for said dependent variable-i for each member of sample-c and in place of each said value of said dependent variable-k in calibration equation-k inserting a value which is functionally related by function-f to said value for said at least one dependent variable-i and selecting an appropriate value for each said at least one constant-k in said calibration equation-k to define a calibration equation-k; wherein said calibration equation-k in conjunction with said at least one spectral feature-k and the inverse of function-f functionally define each predicted value corresponding to each dependent variable-k for each member c, of sample-c, wherein a sum of each absolute difference between each said predicted value and said dependent variable-i for each member c, of sample-c is minimized at least so that said calibration equation-k predicts a value for property-p of each unknown sample that has a value for property-p within a range of interest with a standard error of prediction not substantially greater than a standard error value selected from the group consisting of a standard error of estimate and a standard error of prediction wherein at least one of said standard errors is necessarily present in a direct method used to determine values for property-p to obtain directly or indirectly calibration equation-i; and (2) obtaining spectral data-k for said sample-u by means of instrument-k, and determining a value-u for each spectral feature-u, and defining in conjunction with said calibration equation-k a value for dependent variable-u which when transformed by inverse function-f yields a value for property-p of sample-u.

2. The indirect method of claim 1, wherein said value-k and -i for a material at wavelength-j has a value selected from the group consisting of an absorbance at wavelength-j of electromagnetic radiation, and an arithmetic transform of such an absorbance.

3. In the indirect method of claim 1, the further improvement of applying a slope and bias correction, said applying a slope and bias correction comprising the steps of: determining values for m and b, which substantially satisfy the following expressions:

$$m = \{(\Sigma_c Y_c^a \Sigma_c Y_c^k)/I - \Sigma_c(Y_c^a Y_c^k)\} / \{\{\Sigma_c Y_c^k \Sigma_c Y_c^k\}/I - \Sigma_c Y_c^k Y_c^k\}$$
$$b = \{\Sigma_c Y_c^a - m \Sigma_c Y_c^k\}/I$$

where:

$Y_c^a$ is selected from the group of values consisting of a directly determined value for property-p of a particular member c, of sample-p, a predicted value for property-p of a particular member c, of sample-p by means of a calibration equation for property-p in range of interest, and a combination thereof;

I is the number of members of sample-p;

substitute said values for m and b into the following expression resulting in a further improved calibration equation for the dependent variable-k for instrument-k, which is as follows:

$$\hat{Y}_c^k = \{mA^k + b\} + \Sigma_j \{mB_j^k X_{jc}^k\};$$

whereby an improved calibration equation over that originally determined without the slope and bias correction is achieved.

4. The indirect method of claim 1, wherein at least one of said calibration equation-i and calibration equation-k is determined by applying a method selected from the group of methods consisting of inverse least squares, classical least squares, partial least squares, principal component regression, and a combination of methods selected from the group consisting of inverse least squares, classical least squares, partial least squares, and principal component regression.

5. In a method of claim 1, wherein said member c is selected from the group consisting of isooctane, n-decane, 1-octene, 2,3,4-trimethylpentane, n-heptane cyclohexane, n-hexane, and toluene.

6. The indirect method of claim 1, wherein: said at least one constant-i in calibration equation-i corresponds to at least one slope constant-i, $B_j^i$; said at least one independent variable-i in calibration equation-i corresponds to $X_{js}^i$ where j identifies term for wavelength-j and s identifies a member of sample-s; and said dependent variable-i in calibration equation-i corresponds to $Y_s^i$, wherein: said at least one constant-k in calibration equation-k corresponds to at least one intercept constant-k, $A^k$, and at least one slope constant-k, $B_j^k$; said at least one independent variable-k in calibration equation-k for instrument-k corresponds to $X_{js}^k$ where j identifies term for wavelength-j and s, a member of sample-s; and said dependent variable-k in calibration equation-k corresponds to $Y_s^k$; and wherein: said calibration equation-i and calibration equation-k are linear in form and function-f is selected from the group of functions consisting of: $Y_s^k = mY_s^i + p$, where m is a constant not equal to zero and p is a constant; $Y_s^k = \log$ of $Y_s^i$; and a linear combination thereof.

7. The indirect method of claim 6, wherein at least one of said calibration equation-i and calibration equation-k is determined by applying a method selected from the group of methods consisting of inverse least squares, classical least squares, partial least squares, principal component regression, and a combination of methods selected from the group consisting of inverse least squares, classical least squares, partial least squares, and principal component regression.

8. The indirect method of claim 1, wherein said property-p is a property selected from the group consisting of octane and cetane, and said spectral data-k and -i, respectively, each correspond to absorbances for frequencies in a range of about 800 to about 2500 nanometers.

9. The method of claim 8, wherein said value-k and value-i are functionally determined from spectral data-k and -i by applying a function to said spectral data-k and -i, which function comprises adjacent derivative orders of spectral data for identical wavelengths.

10. The indirect method of claim 8, wherein said spectral features-k and -i, respectively, determined functionally from spectral data-k and -i, comprises determining differentials, respectively, of said spectral data-k and -i.

11. The indirect method of claim 10, wherein said differentials are at least second order and said at least one frequency is selected from the group consisting of at least one methyne band.

12. In the indirect method of claim 10, the further improvement of applying a slope and bias correction, said applying a slope and bias correction comprising the steps of: determining values for m and b, which substantially satisfy the following expressions:

$$m = \{(\Sigma_c Y_c^a \Sigma Y_c^k)/I - \Sigma_c(Y_c^a Y_c^k)\}/\{\{\Sigma_c Y_c^k \Sigma_c Y_c^k\}/I - \Sigma_c Y_c^k Y_c^k\}$$

$$b = \{\Sigma_c Y_c^a - m\Sigma_c Y_c^k\}/I$$

where:

$Y_c^a$ is selected from the group of values consisting of a directly determined value for property-p of a particular member c, of sample-p, a predicted value for property-p of a particular member c, of sample-p by means of a calibration equation for property-p in range of interest, and a combination thereof;

n is the number of members of sample-p;

substitute said values for m and b into the following expression resulting in a further improved calibration equation for the dependent variable-k for instrument-k, which is as follows:

$$\hat{Y}_c^k = \{mA^k + b\} + \Sigma_j\{mB_j^k X_{jc}^k\};$$

whereby an improved calibration equation over that originally determined without the slope and bias correction is achieved.

13. In an indirect method for determining a property-p for a sample-u, using spectral data-k measured by an instrument-k, capable of determining such spectral data-k for said sample-u, in combination with a calibration equation-k, having at least one constant-k, a dependent variable-k, and at least one independent variable-k; wherein each value for said dependent variable-k is determined specifically by particular values for each said at least one independent variable-k, and wherein each said at least one independent variable-k has a value-k equal to a spectral feature-k, functionally determined by said spectral data-k, wherein the improvement comprises:

(1) Defining said calibration equation-k by recourse to a calibration equation-i for instrument-i, wherein said calibration equation-i has at least one constant-i; at least one independent variable-i; and a dependent variable-i; wherein each value for said dependent variable-i is determined specifically by specific values for each said at least one independent variable-i, and wherein each said at least one independent variable-i has a value-i equal to a spectral feature-i, functionally determined from spectral data-i, and wherein calibration equation-i and -k determine, respectively, values for each said dependent variable-k and -i, that are functionally related to one another by a function-f that transforms dependent variable-i into dependent variable-k; for property-p; said method for defining said calibration equation-k by recourse to said calibration equation-i comprising:

(a) obtaining a calibration equation for said instrument-i and assuming a calibration equation-k for said instrument-k has the following form: $Y_s^k = A^k + \Sigma_j\{B_j^k X_{js}^k\}$ and calibration equation-i has the same or different form: where:

$Y_s^i$ is a dependent variable-i in calibration equation-i, and $Y_s^k$ is functionally related to $Y_s^i$ by a function-f;

$A^k$ and $A^i$ are each intercept constants-i and -k in calibration equations-i and -k, respectively;

$X_{js}^i$ and $X_{js}^k$ are each one of said at least one independent variable-i and -k in calibration equations-i and -k, respectively, having a value equal to at least one said spectral feature-i and -k, respectively, of a member s, at wavelength-j; and $B_j^i$ and $B_j^k$ are slope constants-i and -k, respectively, corresponding to coefficients for each of said at least one of independent variable-i and -k at wavelength-j, respectively;

(b) obtaining with instrument-i and -k, spectral data-i and -k, respectively, for each member of a sample-c comprising at least one member c, thereby uniquely determining value-k and -i, respectively, equal to said at least one spectral feature-k and-i, respectively, for each member of sample-c used in step (c);

(c) determining said intercept constant-k and said at least one slope constant-k corresponding respectively to $A^k$ and $B_j^k$ which substantially minimizes the following expression: $\Sigma_c(Y_c^i - A^k - \Sigma_j B_j^k X_{jc}^k)^2$; whereby a calibration equation-k for instrument-k is obtained by reference to said calibration equation for instrument-i; and (2) obtaining spectral data-u for said sample-u by means of instrument-k, and determining functionally a value-u for each spectral feature-u therein; wherein each said value-u is used in combination with said calibration equation-k to determine a value for dependent variable-k, $Y_u^k$, for sample-u which is functionally related by the inverse of function-f to said property-p of said sample-u.

14. In the indirect method of claim 13, the further improvement of applying a slope and bias correction, said applying a slope and bias correction comprising the steps of: determining values for m and b, which substantially satisfy the following expressions:

$$m = \{(\Sigma_c Y_c^a \Sigma Y_c^k)/I - \Sigma_c(Y_c^a Y_c^k)\}/\{\{\Sigma_c Y_c^k \Sigma_c Y_c^k\}/I - \Sigma_c Y_c^k Y_c^k\}$$

$$b = \{\Sigma_c Y_c^a - m\Sigma_c Y_c^k\}/I$$

where:
$Y_c^a$ is selected from the group of values consisting of selected from the group of values consisting of a directly determined value for property-p of a particular member c, of sample-p, a predicted value for property-p of a particular member c, of sample-P by means of a calibration equation for property-p in range of interest, and a combination thereof;
I is the number of members of sample-p;
substitute said values for m and b into the following expression resulting in a further improved calibration equation for the dependent variable-k for instrument-k, which is as follows:

$$\hat{Y}_c^k = \{mA^k + b\} + \Sigma_j\{mB_j^k X_{jc}^k\};$$

whereby an improved calibration equation over that originally determined without the slope and bias correction is achieved.

15. The indirect method of claim 13, wherein at least one of said calibration equation-i and calibration equation-k is determined by applying a method selected from the group of methods consisting of inverse least squares, classical least squares, partial least squares, principal component regression, and a combination of methods selected from the group consisting of inverse least squares, classical least squares, partial least squares, and principal component regression.

16. In a method of claim 13, wherein said member c is selected from the group consisting of isooctane, n-decane, 1-octene, 2,3,4-trimethylpentane, n-heptane cyclohexane, n-hexane, and toluene.

17. The method of claim 13 wherein said property-p is a property selected from the group consisting of octane and cetane, and said spectral data-k and -i, respectively, each correspond to absorbances for frequencies in a range of about 800 to about 2500 nanometers.

18. In the indirect method of claim 17, the further improvement of applying a slope and bias correction, said applying a slope and bias correction comprising the steps of: determining values for m and b, which substantially satisfy the following expressions:

$$m = \{(\Sigma_c Y_c^a \Sigma Y_c^k)/I - \Sigma_c(Y_c^a Y_c^k)\}/\{\{\Sigma_c Y_c^k \Sigma_c Y_c^k\}/I - \Sigma_c Y_c^k Y_c^k\}$$

$$b = \{\Sigma_c Y_c^a - m\Sigma_c Y_c^k\}/I$$

where:
$Y_c^a$ is selected from the group of values consisting of a directly determined value for property-p of a particular member c, of sample-p, a predicted value for property-p of a particular member c, of sample-p by means of a calibration equation for property-p in range of interest, and a combination thereof;
I is the number of members of sample-p;
substitute said values for m and b into the following expression resulting in a further improved calibration equation for the dependent variable-k for instrument-k, which is as follows:

$$\hat{Y}_c^k = \{mA^k + b\} + \Sigma_j\{mB_j^k X_{jc}^k\};$$

Whereby an improved calibration equation over that originally determined without the slope and bias correction is achieved.

19. In an indirect method for determining a property-p for a sample-u, using spectral data-k measured by an instrument-k, capable of determining such spectral data-k for said sample-u, in combination with a calibration equation-k, having at least one constant-k, a dependent variable-k, and at least one independent variable-k; wherein each value for said dependent variable-k is determined specifically by specific values for each said at least one independent variable-k, and wherein each said at least one independent variable-k has a value-k equal to a spectral feature-k, functionally determined by said spectral data-k; wherein the improvement comprises:

(1) defining said calibration equation-k by recourse to a calibration equation-i for instrument-i, wherein said calibration equation-i has: at least one constant-i comprising an intercept constant-i and at least one slope constant-i; at least one independent variable-i; and a dependent variable-i; wherein each value for said dependent variable-i is determined specifically by specific values for each said at least one independent variable-i, and wherein each said at least one independent variable-i has a value-i equal to a spectral feature-i, functionally determined from spectral data-i, and wherein calibration equation-i and -k determine, respectively, values for each said dependent variable-k and -i, that are functionally related to one another by a function-f that transforms dependent variable-i into dependent variable-k; said method for defining said calibration equation-k by recourse to said calibration equation-i comprising:

(a) obtaining a calibration equation for said instrument-i for property-p, and assuming a calibration equation-k for said instrument-k; wherein each have the following form:

$$Y_s^i = A^i + \Sigma_j\{B_j^i X_{js}^i\}$$

and $$Y_s^k = A^k + \Sigma_j\{B_j^k X_{js}^k\}$$

where:
$Y_s^i$ is the dependent variable-i for member s in calibration equation-i and $Y_s^k$ is functionally related to $Y_s^i$ by a function-f;
$A^k$ and $A^i$ are each intercept constants-i and -k in calibration equations-i and -k, respectively;
$X_{js}^i$ and $X_{js}^k$ are each one of said at least one independent variable-i and -k in calibration equations-i and -k, respectively, each having a value equal to at least one said spectral feature-i and -k, respectively, of each member s, of sample-s at wavelength-j; and
$B_j^i$ and $B_j^k$ are slope constants-i and -k, respectively, corresponding to coefficients for each of said at least one of independent variables-i and -k at wavelength-j, respectively;

(b) obtaining with instrument-i and -k, spectral data-i and -k, respectively, for each member of a sample-c comprising at least one member c, and functionally determining value-k and -i, respectively, equal to said at least one spectral feature-k and -i, respectively, for each member of sample-c used in step (c);

(c) determining values of $B_j^k$ and $A^k$ so that the following two equations are simultaneously substantially satisfied: $B_j^k = B_j^i \Sigma_c X_{jc}^i X_{jc}^k / \Sigma_c (X_{jc}^k)^2$ and $A^k = \Sigma_c (Y_c^i - \Sigma_j B_j^k X_{jc}^k)/n$; where n=number of members to sample-c; whereby a calibration equation-k for instrument-k is obtained by reference to said calibration equation for instrument-i; and (2) obtaining spectral data-u by means of instrument-k for said sample-u, and functionally determining a value-u for each spectral features-u therein; wherein each said value-u is used in combination with said calibration equation-k to determine a value for dependent variable-k, $Y_u^k$, for sample-u which is functionally related by the inverse of function-f to said property-p of said sample-u.

20. In the indirect method of claim 19, the further improvement of applying a slope and bias correction, said applying a slope and bias correction comprising the steps of: determining values for m and b, which substantially satisfy the following expressions:

$$m = \{(\Sigma_c Y_c^a \Sigma Y_c^k)/I - \Sigma_c (Y_c^a Y_c^k)\} / \{(\Sigma_c Y_c^k)/I - \Sigma_c Y_c^k Y_c^k\}$$

$$b = \{\Sigma_c Y_c^a - m\Sigma_c Y_c^k\}/I$$

where:
$Y_c^a$ is selected from the group of values consisting of a directly determined value for property-p of a particular member c, of sample-p, a predicted value for property-p of a particular member c, of sample-p by means of a calibration equation for property-p in range of interest, and a combination thereof;

I is the number of members of sample-p;

substitute said values for m and b into the following expression resulting in a further improved calibration equation for the dependent variable-k for instrument-k, which is as follows:

$$\hat{Y}_c^k = \{mA^k + b\} + \Sigma_j \{mB_j^k X_{jc}^k\};$$

whereby an improved calibration equation over that originally determined without the slope and bias correction is achieved.

21. The indirect method of claim 19, wherein at least one of said calibration equation-i and calibration equation-k is determined by applying a method selected from the group of methods consisting of inverse least squares, classical least squares, partial least squares, principal component regression, and a combination of methods selected from the group consisting of inverse least squares, classical least squares, partial least squares, and principal component regression.

22. In an indirect method for determining a property-p for a sample-u, using spectral data-k measured by an instrument-k, capable of determining such spectral data-k for said sample-u in combination with a calibration equation-k, having at least one constant-k, a dependent variable-k, and at least one independent variable-k; wherein each value for said dependent variable-k is determined specifically by specific values for each said at least one independent variable-k, and wherein each said at least one independent variable-k has a value-k equal to a spectral feature-k, uniquely determined by reference to said spectral data-k; wherein the improvement comprises:

(1) defining said calibration equation-k by recourse to a calibration equation-i for instrument-i, wherein said calibration equation-i has: at least one constant-i; at least one independent variable-i; and a dependent variable-i; wherein each value for said dependent variable-i is determined specifically by specific values for each said at least one independent variable-i, and wherein each said at least one independent variable-i has a value-i equal to a spectral feature-i, functionally determined from spectral data-i, and wherein calibration equation-i and -k determine, respectively, values for each said dependent variable-k and -i, that are functionally related to one another by a function-f that transforms dependent variable-i into dependent variable-k; said method for defining said calibration equation-k by recourse to said calibration equation-i comprising:

(a) obtaining a calibration equation for said instrument-i for property-p, and assuming a calibration equation-k for said instrument-k wherein each have the following form:

$$Y_s^i = A^i + \Sigma_j \{B_j^i X_{js}^i\}$$

and $$Y_s^k = A^k + \Sigma_j \{B_j^k X_{js}^k\}$$

where:
$Y_s^i$ is the dependent variable-i in calibration equation-i, and $Y_s^k$ is functionally related to $Y_s^i$ by a function-f;

$A^k$ and $A^i$ are each intercepts constants-i and -k in calibration equations-i and -k, respectively;

$X_{js}^i$ and $X_{js}^k$ are each one of said at least one independent variable-i and -k in calibration equations-i and -k, respectively, each having a value equal to at least one said spectral feature-i and -k, respectively; and $B_j^i$ and $B_j^k$ are slope constants-i and -k, respectively, corresponding to coefficients for each of said at least one of independent variables-i and -k corresponding to spectral features-i and -k at least one wavelength-j, respectively;

(b) obtaining with instrument-i and -k, spectral data-i and -k, respectively, for each member of a sample-s comprising at least one member c, used in step (c), thereby uniquely determining value-k and -i, respectively, equal to said at least one spectral feature-k and -i, respectively, for each member of sample-c having a total of n members;

(c) determining said intercept constant-k and said at least one slope constant-k corresponding, respectively, to values of $B_j^k$ and $A^k$ so that the following are substantially satisfied: $B_j^k = B_j^i \Sigma_c X_{jc}^i / \Sigma_c (X_{jc}^k)$ and $A^k = \Sigma_c (Y_c^i - \Sigma_j B_j^k X_{jc}^k)/n$; whereby a calibration equation-k for instrument-k is obtained by reference to said calibration equation for instrument-i;

(2) obtaining spectral data-u for said sample-u by means of instrument-k, and determining functionally a value-u for each spectral feature-u therein; wherein each said value-u is used in combination with said calibration equation-k to determine a value for dependent variable-k, $Y_u{}^k$, for sample-u which is functionally related by the inverse of function-f to said property-p of said sample-u.

23. In the indirect method of claim 22, the further improvement of applying a slope and bias correction, said applying a slope and bias correction comprising the steps of: determining values for m and b, which substantially satisfy the following expressions:

$$m=\{(\Sigma_c Y_c{}^a \Sigma Y_c{}^k)/I - \Sigma_c(Y_c{}^a Y_c{}^k)\}/\{\{\Sigma_c Y_c{}^k \Sigma_c Y_c{}^k\}/I - \Sigma_c Y_c{}^k Y_c{}^k\}$$

$$b = \{\Sigma_c Y_c{}^a - m \Sigma_c Y_c{}^k\}/I$$

where:
$Y_c{}^a$ is selected from the group of values consisting of a directly determined value for property-p of a particular member c, of sample-p, a predicted value for property-p of a particular member c, of sample-p by means of a calibration equation for property-p in range of interest, and a combination thereof;
I is the number of members of sample-p;
substitute said values for m and b into the following expression resulting in a further improved calibration equation for the dependent variable-k for instrument-k, which is as follows:

$$\hat{Y}_c{}^k = \{mA^k + b\} + \Sigma_j\{mB_j{}^k X_{jc}{}^k\};$$

whereby an improved calibration equation over that originally determined without the slope and bias correction is achieved.

24. The indirect method of claim 22, wherein at least one of said calibration equation-i and calibration equation-k is determined by applying a method selected from the group of methods consisting of inverse least squares, classical least squares, partial least squares, principal component regression, and a combination of methods selected from the group consisting of inverse least squares, classical least squares, partial least squares, and principal component regression.

25. In a method for recalibrating an instrument-k in light of its former calibrated condition as instrument-i or for calibrating instrument-k, previously uncalibrated, in light of a calibrated instrument-i wherein a calibrated instrument is one having a particular calibration equation, here calibration equation-k, based upon which equation spectraldata of a sample can be used to predict a physical or chemical property of said sample, the improvement which comprises: determining said calibration equation-k by means of a calibration equation-i, each said calibration equation-k and -i, respectively, having: at least one constant-k and -i; a dependent variable-k and -i; and at least one independent variable-k and -i; wherein each value, respectively, for said dependent variable-k and -i is determined specifically by particular values for each said at least one independent variable-k and -i and wherein each said at least one independent variable-k and -i has respectively a value-k and -i equal to a spectral feature-k and -i, functionally determined, respectively, by spectral data-k and -i, determined respectively, by an instrument-k and -i capable of determining, respectively, said spectral data-k and -i for a sample, s; said method comprising:

(a) obtaining respectively with instrument-i and instrument-k spectral data-i and spectral data-k, respectively, for each member of a sample-c, comprising at least one member c, thereby functionally determining value-k and value-i, respectively, equal to said at least one spectral feature-k and said at least one spectral feature-i, respectively, for each member of sample-c used in step (b);

(b) determining in accordance with calibration equation-i, a value for said dependent variable-i for each member of sample-c and in place of each said value of said dependent variable-k in calibration equation-k inserting a value which is related by a function-f to each said value for said dependent variable-i and selecting an appropriate value for each said at least one constant-k in said calibration equation-k to produce a calibration equation-k; wherein said calibration equation-k in conjunction with said at least one spectral feature-k and the inverse of function-f functionally define each predicted value corresponding to each dependent variable-k for each member c, of sample-c, wherein a sum of absolute differences between each said predicted value and said dependent variable-i for each member c, of sample-c is minimized at least so that said calibration equation-k predicts a value for property-p of each unknown sample that has a value for property-p within a range of interest with a standard error of prediction not substantially greater than a standard error value selected from the group consisting of a standard error of estimate and a standard error of prediction wherein at least one of said standard errors is necessarily present in a direct method used to determine values for property-p to obtain directly or indirectly calibration equation-i.

26. In the method of claim 25, the further improvement of applying a slope and bias correction, said applying a slope and bias correction comprising the steps of: determining values for m and b, which substantially satisfy the following expressions:

$$m=\{(\Sigma_c Y_c{}^a \Sigma Y_c{}^k)/I - \Sigma_c(Y_c{}^a Y_c{}^k)\}/\{\{\Sigma_c Y_c{}^k \Sigma_c Y_c{}^k\}/I - \Sigma_c Y_c{}^k Y_c{}^k\}$$

$$b = \{\Sigma_c Y_c{}^a - m \Sigma_c Y_c{}^k\}/I$$

where:
$Y_c{}^a$ is selected from the group of values consisting of a directly determined value for property-p of a particular member c, of sample-p, a predicted value for property-p of a particular member c, of sample-p by means of a calibration equation for property-p in range of interest, and a combination thereof;
n is the number of members of sample-p;
substitute said values for m and b into the following expression resulting in a further improved calibration equation for the dependent variable-k for instrument-k, which is as follows:

$$\hat{Y}_c{}^k = \{mA^k + b\} + \Sigma_j\{mB_j{}^k X_{jc}{}^k\};$$

whereby an improved calibration equation over that originally determined without the slope and bias correction is achieved.

27. The method of claim 25, wherein at least one of said calibration equation-i and calibration equation-k is determined by applying a method selected from the group of methods consisting of inverse least squares, classical least squares, partial least squares, principal component regression, and a combination of methods selected from the group consisting of inverse least squares, classical least squares, partial least squares, and principal component regression.

28. The method of claim 25, wherein said calibration equations for said instrument-i, and said instrument-k, each have the following linear form:

$$Y_s^i = A^i + \Sigma_j \{B_j^i X_{js}^i\}$$

and $$Y_s^k = A^k + \Sigma_j \{B_j^k X_{js}^k\}$$

where:
$Y_s^i$ is the dependent variable-i in calibration equation-i and $Y_s^k$ is functionally related to $Y_s^i$ by a function-f;
$A^k$ and $A^i$ are each intercept constants-i and -k in calibration equations-i and -k, respectively;
$X_{js}^i$ and $X_{js}^k$ are each one of said at least one independent variable-i and -k in calibration equations-i and -k, respectively, having a value equal to at least one said spectral feature-i and -k, respectively of a member s, at wavelength-j; and
$B_j^i$ and $B_j^k$ are slope constants-i and -k, respectively, corresponding to coefficients for each said at least one independent variable-i and -k corresponding to spectral features-i and -k at wavelength-j, respectively;
(a) obtaining with instrument-i and -k, spectral data-i and -k, respectively, for each member of a sample-c comprising at least one member c, thereby functionally determining value-k and -i, respectively, equal to said at least one spectral feature-k and-i, respectively, for each member c, of sample-c used in step (b); and
(b) determining said intercept constant-k, and said at least one slope constant-k corresponding respectively to $B_j^k$ and $A^k$ which substantially minimizes the following expression: $\Sigma_c(Y_c^{i} - A^k - \Sigma_j B_j^k X_{jc}^k)^2$
whereby a method is provided for recalibrating instrument-k in light of its former calibrated condition as instrument-i.

29. The method of claim 28, wherein at least one of said calibration equation-i and calibration equation-k is determined by applying a method selected from the group of methods consisting of inverse least squares, classical least squares, partial least squares, principal component regression, and a combination of methods selected from the group consisting of inverse least squares, classical least squares, partial least squares, and principal component regression.

30. The method of claim 25, wherein said spectral data-k and -i is in the form of electromagnetic radiation selected from a group of electromagnetic radiation consisting of: ultraviolet, visible, near-infrared, mid-infrared, far-infrared, microwave, and radiowave.

31. In the method claim 30 the further improvement of applying a slope and bias correction, said applying a slope and bias correction comprising the steps of: determining values for m and b, which substantially satisfy the following expressions:

$$m = \{(\Sigma_c Y_c^a \Sigma Y_c^k)/I - \Sigma_c(Y_c^a Y_c^k)\} / \{\{\Sigma_c Y_c^k \Sigma_c Y_c^k\} /I - \Sigma_c Y_c^k Y_c^k\}$$

$$b = \{\Sigma_c Y_c^a - m \Sigma_c Y_c^k\}/I$$

where:
$Y_c^a$ is selected from the group of values consisting of a directly determined value for property-p of a particular member c, of sample-p, a predicted value for property-p of a particular member c, of sample-p by means of a calibration equation for property-p in range of interest, and a combination thereof;
I is the number of members of sample-p;
substitute said values for m and b into the following expression resulting in a further improved calibration equation for the dependent variable-k for instrument-k, which is as follows:

$$\hat{Y}_c^k = \{mA^k + b\} + \Sigma_j\{mB_j^k X_{jc}^k\};$$

whereby an improved calibration equation over that originally determined without the slope and bias correction is achieved.

32. In the method of claim 25, wherein said value-k and value-i are functionally determined from spectral data-k and -i by applying a function to said spectral data-k and -i, which function is selected from the group consisting of:
first, second, third, forth, fifth, and higher derivatives of spectral data.

33. In the method of 32, the further improvement of applying a slope and bias correction, said applying a slope and bias correction comprising the steps of: determining values for m and b, which substantially satisfy the following expressions:

$$m = \{(\Sigma_c Y_c^a \Sigma Y_c^k)/I \Sigma_c(Y_c^a Y_c^k)\} / \{\{\Sigma_c Y_c^k \Sigma_c Y_c^k\} /I - \Sigma_c Y_c^k Y_c^k\}$$

$$b = \{\Sigma_c Y_c^a - m \Sigma_c Y_c^k\}/I$$

where:
$Y_c^a$ is selected from the group of values consisting of a directly determined value for property-p of a particular member c, of sample-p, a predicted value for property-p of a particular member c, of sample-p by means of a calibration equation for property-p in range of interest, and a combination thereof;
I is the number of members of sample-p;
substitute said values for m and b into the following expression resulting in a further improved calibration equation for the dependent variable-k for instrument-k, which is as follows:

$$\hat{Y}_c^k = \{mA^k + b\} + \Sigma_j\{mB_j^k X_{jc}^k\};$$

whereby an improved calibration equation over that originally determined without the slope and bias correction is achieved.

34. The method of claim 25, wherein: said calibration equation-i and calibration equation-k are linear in form.

35. In the method of claim 34, the further improvement of applying a slope and bias correction, said applying a slope and bias correction comprising the steps of: determining values for m and b, which substantially satisfy the following expressions:

$$m = \{(\Sigma_c Y_c^a \Sigma Y_c^k)/I - \Sigma_c(Y_c^a Y_c^k)\} / \{\{\Sigma_c Y_c^k \Sigma_c Y_c^k\} /I - \Sigma_c Y_c^k Y_c^k\}$$

$$b = \{\Sigma_c Y_c^a - m\Sigma_c Y_c^k\}/I$$

where:
- $Y_c^a$ is selected from the group of values consisting of a directly determined value for property-p of a particular member c, of sample-p, a predicted value for property-p of a particular member c, of sample-p by means of a calibration equation for property-p in range of interest, and a combination thereof;
- I is the number of members of sample-p;

substitute said values for m and b into the following expression resulting in a further improved calibration equation for the dependent variable-k for instrument-k, which is as follows:

$$\hat{Y}_c^k = \{mA^k + b\} + \Sigma_j\{mB_j^k X_{jc}^k\};$$

whereby an improved calibration equation over that originally determined without the slope and bias correction is achieved.

36. In a method of claim 34, wherein said member c is selected from the group consisting of isooctane, n-decane, 1-octene, 2,3,4,-trimethylpentane, n-heptane, cyclohexane, n-hexane, and toluene.

37. The method of claim 25, wherein said calibration equations for said instrument-i, and said instrument-k, each have the following linear form:

$$Y_s^i = A^i + \Sigma_j\{B_j^i X_{js}^i\}$$

and $$Y_s^k = A^k + \Sigma_j\{B_j^k X_{js}^k\}$$

where:
- $Y_s^i$ is the dependent variable-i in calibration equation-i and $Y_s^k$ is functionally related to $Y_s^i$ by a function-f;
- $A^k$ and $A^i$ are each intercept constants-i and -k in calibration equations-i and -k, respectively;
- $X_{js}^i$ and $X_{js}^k$ are each one of said at least one independent variable-i and -k in calibration equations-i and -k, respectively, having a value equal to at least one said spectral feature-i and -k, respectively of a member s, at wavelength-j; and
- $B_j^i$ and $B_j^k$ are slope constants-i and -k, respectively, corresponding to coefficients for each said at least one independent variable-i and -k corresponding to spectral features-i and -k at wavelength-j, respectively;

(a) determining by measuring respectively with instrument-i and -k, spectral data-i and -k, respectively, for each member of a sample-c comprising at least one member c, thereby functionally determining value-k and -i, respectively, equal to said at least one spectral feature-k and-i, respectively, for each member c, of sample-c used in step (b); and (b) determining said intercept constant-k and said at least one slope constant-k corresponding, respectively, to $B_j^k$ and $A^k$ which substantially satisfy the following two equations simultaneously: $B_j^k = B_j^i \Sigma_c X_{jc}^i X_{jc}^k / \Sigma_c (X_{jc}^k)^2$ and $A^k = \Sigma_c (Y_c^k - \Sigma_j B_j^k X_{jc}^k)/n$; where n=number of members of sample-c;

whereby a method is provided for recalibrating instrument-k in light of its former calibrated condition as instrument-i or for calibrating instrument-k, previously uncalibrated, in light of a calibrated instrument-i.

38. The method of claim 37, wherein at least one of said calibration equation-i and calibration equation-k is determined by applying a method selected from the group of methods consisting of inverse least squares, classical least squares, partial least squares, principal component regression, and a combination of methods selected from the group consisting of inverse least squares, classical least squares, partial least squares, and principal component regression.

39. The method of claim 37, wherein said property-p is a property selected from the group consisting of octane and cetane, and said spectral data-k and -i, respectively, each correspond to absorbances for frequencies in a range of about 800 to about 2500 nanometers.

40. The method of claim 25, wherein said calibration equations for said instrument-i and said instrument-k each have the following linear form:

$$Y_s^i = A^i + \Sigma_j\{B_j^i X_{js}^i\}$$

and $$Y_s^k = A^k + \Sigma_j\{B_j^k X_{js}^k\}$$

where:
- $Y_s^i$ is the dependent variable-i in calibration equation-i and $Y_s^k$ is functionally related to $Y_s^i$ by a function-f;
- $A^k$ and $A^i$ are each intercept constants-i and -k in calibration equations-i and -k, respectively;
- $X_{js}^i$ and $X_{js}^k$ are each one of said at least one independent variable-i and -k in calibration equations-i and -k, respectively, having a value equal to at least one said spectral feature-i and -k, respectively of a member s, at wavelength-j; and
- $B_j^i$ and $B_j^k$ are slope constants-i and -k, respectively, corresponding to coefficients for each said at least one independent variable-i and -k corresponding to spectral features-i and -k at wavelength-j, respectively;

(a) obtaining with instrument-i and -k, spectral data-i and -k, respectively, for each member of a sample-c comprising at least one member c, thereby functionally determining value-k and -i, respectively, equal to said at least one spectral feature-k and-i, respectively, for each member c, of sample-c used in step (b); and (b) determining values of $B_j^k$ and $A^k$ which substantially satisfy the following two equations simultaneously: $B_j^k = B_j^i \Sigma_c X_{jc}^i X_{jc}^k / \Sigma_c (X_{jc}^k)^2$ and $A^k = \Sigma_c (Y_c^k - \Sigma_j B_j^k X_{jc}^k)/n$; where n=number of members of sample-c;

whereby a method is provided for recalibrating instrument-k in light of its former calibrated condition as instrument-i or for calibrating instrument-k, previously uncalibrated, in light of a calibrated instrument-i.

41. In the method of claim 40, the further improvement of applying a slope and bias correction, said applying a slope and bias correction comprising the steps of: determining values for m and b, which substantially satisfy the following expressions:

$$m = \{(\Sigma_c Y_c^a \Sigma Y_c^k)/I - \Sigma_c (Y_c^a Y_c^k)\} / \{\{\Sigma_c Y_c^k \Sigma_c Y_c^k\}/I - \Sigma_c Y_c^k Y_c^k\}$$

$$b = \{\Sigma_c Y_c^a - m\Sigma_c Y_c^k\}/I$$

where:

$Y_c^a$ is selected from the group of values consisting of a directly determined value for property-p of a particular member c, of sample-p, a predicted value for property-p of a particular member c, of sample-p by means of a calibration equation for property-p in range of interest, and a combination thereof;

n is the number of members of sample-p;

substitute said values for m and b into the following expression resulting in a further improved calibration equation for the dependent variable-k for instrument-k, which is as follows:

$$\hat{Y}_c^k = \{mA^k + b\} + \Sigma_j \{mB_j^k X_{jc}^k\};$$

whereby an improved calibration equation over that originally determined without the slope and bias correction is achieved.

42. The method of claim 40, wherein at least one of said calibration equation-i and calibration equation-k is determined by applying a method selected from the group of methods consisting of inverse least squares, classical least squares, partial least squares, principal component regression, and a combination of methods selected from the group consisting of inverse least squares, classical least squares, partial least squares, and principal component regression.

43. The method of claim 40, wherein said property-p is a property selected from the group consisting of octane and cetane, and said spectral data-k and -i, respectively, each correspond to absorbances for frequencies in a range of about 800 to about 2500 nanometers.

44. In a method of claim 25, wherein said member c is selected from the group consisting of isooctane, n-decane, 1-octene, 2,3,4-trimethylpentane, n-heptane cyclohexane, n-hexane, and toluene.

45. The method of claim 25, wherein said property-p is a property selected from the group consisting of octane and cetane, and said spectral data-k and -i, respectively, each correspond to absorbances for frequencies in a range of about 800 to about 2500 nanometers.

46. In a method of claim 45, wherein said member c is selected from the group consisting of pure components of a hydrocarbon fuel.

47. In a method of claim 45, wherein said member c is selected from the group consisting of isooctane, n-decane, 1-octene, 2,3,4-trimethylpentane, cyclohexane, n-hexane, and toluene.

48. In a method of claim 45, wherein said member c is selected from the group consisting of paraffin, isoparaffin, aromatic, naphthene, and olefin.

49. In a method of claim 48, wherein said paraffin is selected from the group consisting of hexane and heptane; said isoparaffin is selected from the group consisting of 2,3-dimethylbutane, 2,3,4-trimethylpentane, and isooctane; said aromatic is selected from the group consisting of ethyl benzene, S-butyl benzene, and t-butyl benzene; said naphthene is 1,2-dimethylclycohexene, as either a cis- or trans-isomer; and said olefin is 1-octene as either a cis- or trans isomer.

50. In an indirect method for determining a property-p for a sample-u by measuring and using spectral data-(ku) measured by an instrument-k capable of measuring such spectral data-(ku) for said sample-u in conjunction with a calibration equation-k, wherein said calibration equation-k defines a dependent-variable-(ku), in terms of at least one constant-k and at least one independent-variable-(kju), wherein said at least one independent-variable-(kju) has a value equal to at least one spectral-feature-(kju) determined from said spectral data-(ku) for said sample-u by a first functions that involves wavelength-j, and wherein said dependent-variable-(ku) has a value substantially equal to said property-p for said sample-u when values for each said at least one constant-k and each said at least one independent-variable-(kju) are substituted appropriately into said calibration equation-k; wherein the improvement comprises:

determining a value for each said at least one constant-k by recourse to a calibration equation-i, wherein said calibration equation-i defines dependent-variable-(ic) as a function of an independent-variable-(ijc) which independent-variable-(ijc) is equal to a spectral feature-(ijc) functionally determined from spectral data-(ic) corresponding both to member c of a calibration sample-c having a total of n members and to each wavelength-j, and said dependent-variable-(ic) has a value substantially equal to said property-p of said member c, of said sample-c; said determining a value for each said at least one constant-k comprises the steps of:

(1) using respectively spectral data-(ic) and spectral data-(kc) for each member c, of said calibration sample-c measured respectively by instrument-i and instrument-k, to determine each said at least one independent-variable-(kjc) corresponding to each member c, and to determine from said calibration equation-i a value for said dependent-variable-(ic) corresponding to each member c;

(2) maintaining consistent a set of equations that results from substituting in place of the value for dependent-variable-(kc) that value for dependent-variable-(ic), while selecting a value for each said at least one constant-k so that a sum of absolute differences in value between each new-dependent-variable-(kc) and dependent-variable-(ic) corresponding to each said member c, is substantially minimized; wherein said new-dependent-variable-(kc) is determined by calibration equation-k after substituting each selected value for each said at least one constant-k along with each said at least one independent-variable-(kjc) in said calibration equation-k.

51. The improved method of claim 50, wherein said selecting a value for each said at least one constant-k is continued at least until standard error of estimation for property-p is not significantly greater than that standard error of estimation for property-p used to establish calibration equation-i.

52. The improved method of claim 50, wherein said calibration equation-k has the following form which defines and at least one constant-k that comprises an intercept-constant-k and at least one slope-constant-(kj):

$$Y^k_c = A^k + \Sigma_j B^k_j I^k_{jc}$$

wherein:

$Y^k_c$ = dependent-variable-(kc)

$A^k$ = intercept-constant-k $B^k_j$ = slope-constant-(kj); and $I^k_{jc}$ = independent-variable-(kjc);

wherein said selecting each value for each said at least one constant-k comprises selecting at least one intercept-constant-k, $A^k$, and at least one slope-constant-(kj), $B^k_j$, so that the expression immediately following is reduced substantially to its minimum value:

$$\Sigma_c\{Y^i_c-(A^k-\Sigma_j B^k_j I^k_{jc})\}^2.$$

53. The improved method of claim 50, wherein said calibration equation-i is in the same linear form as calibration equation-k and wherein said calibration equation-i defines dependent-variable-(ic) in terms of at least one constant-i and at least one independent-variable-(ijc), wherein said at least one constant-i comprises: an intercept-constant-i, and at least one slope-constant-(ij) involving each wavelength-j used in calibration equation-i; and wherein each said at least one independent-variable-(ijc) has a value substantially equal to each at least one spectral feature-(ijc) determined by said first function from spectral data-(ic) measured by said instrument-i that involves each said wavelength-j for member c; and wherein said dependent-variable-(ic) has a value substantially equal to said property-p for said sample-u when values for each said at least one constant-i and each said at least one independent-variable-(ijc) are appropriately substituted into said calibration equation-i and sample-u is member c, wherein calibration equation-k and calibration equation-i respectively, have the linear forms:

$$Y^i_c = A^i + \Sigma_j B^i_j I^i_{jc}$$

and $$Y^k_c = A^k + \Sigma_j B^k_j I^k_{jc};$$

wherein:
$Y^i_c$ = dependent-variable-(ic)
$A^i$ = intercept-constant-i
$B^i_j$ = slope-constant-(ij); and
$I^i_{jc}$ = independent-variable-(ijc)
$A^k$ = intercept-constant-k
$B^k_j$ = slope-constant-(kj); and
$I^k_{jc}$ = independent-variable-(kjc)

and wherein the following two equations are simultaneously substantially satisfied:

$$B^k_j = \{B^i_j \times \Sigma_c(I^i_{jc} \times I^{kj}_c)\}/\Sigma_c(I^k_{jc})^2$$

and $$A^k = \Sigma_c\{Y^i_c - \Sigma_j B^k_j I^k_{jc}\}/n$$

where n = number of members in calibration sample-c; whereby said calibration equation-k for instrument-k is obtained by reference to said calibration equation-i.

54. The improved method of claim 50, wherein said calibration equation-i is in the same linear form as calibration equation-k and wherein said calibration equation-i defines dependent-variable-(ic) in terms of at least one constant-i and at least one independent-variable-(ijc), wherein said at least one constant-i of calibration equation-i comprises: an intercept-constant-i, and at least one slope-constant-(ij) involving each wavelength-j used in calibration equation-i; and wherein each said at least one independent-variable-(ijc) has a value substantially equal to each at least one spectral feature-(ijc) determined by said first function from spectral data-(ic) measured by instrument-i that involves each said wavelength-j for member c, and wherein said dependent-variable-(ic) has a value substantially equal to said property-p for said member c when values for each said at least one constant-i and each said at least one independent-variable-(ijc) are appropriately substituted into said calibration equation-i; wherein calibration equation-i and calibration equation-k have, respectively, the linear forms:

$$Y^i_c = A^i + \Sigma_j\{B^i_j I^i_{jc}\}$$

$$Y^k_c = A^k + \Sigma_j\{B^k_j I^k_{jc}\}$$

and wherein the following two equations are simultaneously substantially satisfied:

$$B^k_j = B^i_j \Sigma_c I^i_{jc}/\Sigma_c I^k_{jc}$$

and $$A^k = \{\Sigma_c(Y^i_c - \Sigma_j B^k_j I^k_{jc})\}/n;$$

whereby said calibration equation-k for instrument-k is obtained by reference to said calibration equation-i.

55. The improved method of claim 50, wherein there is a further improvement of applying a slope and bias correction comprising the steps of: determining values for m and b, which substantially satisfy the following expressions simultaneously:

$$m = \{\Sigma_c\{Y^a_c \Sigma_c Y^k_c\}/I - \{\Sigma_c Y^a_c Y^k_c\}\}/\{\{\Sigma_c Y^k_c \Sigma_c Y^k_c\}/I - \Sigma_c Y^k_c Y^k_c\}$$

$$b = \{\Sigma_c Y^a_c - m\Sigma_c Y^k_c\}/I$$

where:
$Y^a_c$ = Dependent-variable-(ac) is selected from the group of values consisting of: a directly determined value for property-p of a particular member c, of sample-p; a predicted value for property-p of said member c, of sample-p by means of a calibration equation for property-p in a range of interest; and a combination thereof;
I is the number of members of sample-p; and to apply said slope and bias correction, substitute said values for m and b into the following expression:

$$Y^k_c = \{mA^k + b\} + \Sigma_j\{mB^k_j I^k_{jc}\}$$

whereby an improved calibration equation-k for dependent-variable-(kc) for instrument-k is obtained.

56. The improved method of claim 50, wherein said property-p is selected from the group consisting of octane and cetane and said spectral data-k and -i, respectively, each correspond to at least one absorbance for light radiation with a frequency for each member c, in the range of about 800 to 2500 nanometers.

57. In a method of claim 50, wherein said member c is selected from the group consisting of isooctane, n-decane, 1-octene, 2,3,4-trimethylpentane, n-heptane cyclohexane, n-hexane, and toluene.

58. The improved method of claim 50, wherein instead of a value equal to dependent-variable-(ic), $Y^i_c$, being substituted for that value for dependent-variable-(kc), $Y^k_c$, a mathematically transformed dependent-variable-(ic), $Y^t_c$, which is transformed by means of a function is used to yield a value that is substituted for dependent-variable-(kc) in calibration equation-k.

59. The improved method of claim 58, wherein said mathematically transformed dependent-variable-(ic) value, $Y^t_c$, is determined by a function selected from the group consisting of:

$Y'_c = u \times Y^i_c + v$; $Y'_c = u \times \log Y^i_c + v$; where u is any real number not equal to zero and v is any real number including zero.

60. The improved method of claim 50, wherein said first function to obtain spectral feature-(ic) and spectral feature-(kc), respectively from spectral data-(ic) and spectral data-(kc) for each member c, comprises differentials.

61. The improved method of claim 60, wherein said differentials comprise at least second order.

62. The improved method of claim 61, wherein said wavelength-j includes at least one frequency selected from the group consisting of at least one methyne band.

63. In a method for recalibrating an instrument-k in light of its former calibrated condition as instrument-i or for calibrating instrument-k, previously uncalibrated, in light of a calibrated instrument-i wherein a calibrated instrument is one having a particular calibration equation, here calibration equation-k, based upon which equation spectral data of a sample can be used to predict a physical or chemical property of said sample, the improvement which comprises: determining said calibration equation-k for instrument-k by means of said calibration equation-i for instrument-i, wherein said calibration equation-k defines a dependent-variable-(ku), in terms of at least one constant-k and at least one independent-variable-(kju), wherein said at least one independent-variable-(kju) has a value equal to at least one spectral feature-(kju) determined from said spectral data-(ku) measured by said instrument-k for said sample-u by a first function that involves wavelength-j, and wherein said dependent-variable-(ku) has a value substantially equal to a property-p for said sample-u when values for each said at least one constant-k and each said at least one independent-variable-(kju) are substituted appropriately into said calibration equation-k; wherein said calibration equation-i defines dependent-variable-(iu) as a function of an independent-variable-(iju) which independent-variable-(iju) is equal to a spectral feature-(iju) determined from spectral data-(iu) measured by said instrument-i for said sample-u corresponding to each wavelength-j, and has a value substantially equal to said property-p of said sample-u; said method for determining said calibration equation-k by means of said calibration equation-i comprising:

(1) using respectively spectral data-(ic) and spectral data-(kc) for each member c, of a group of samples having n members that are each measured respectively by said instrument-i and instrument-k, to determine each said at least one independent-variable-(ijc) and independent-variable-(kjc), respectively, involving each wavelength-j corresponding to each member c, and to determine from calibration equation-i a value for said dependent-variable-(ic) corresponding to each member c;

(2) maintaining consistent a set of equations that results from substituting in place of the value for dependent-variable-(kc) that value for dependent-variable-(ic), while selecting a value for each said at least one constant-k so that a sum of absolute differences between each new-dependent-variable-(kc) and dependent-variable-(ic) corresponding to each said member c, is minimized; wherein said each new-dependent-variable-(kc) is determined by calibration equation-k after substituting each selected value for each said at least one constant-k along with each said at least one independent-variable-(kjc) in said calibration equation-k.

64. The method of claim 63, wherein said selecting a value for each said at least one constant-k is continued at least until standard error of estimation for property-p is not significantly greater than that standard of estimation for property-p used to establish calibration equation-i.

65. The method of claim 63, wherein said calibration equation-k has the following form which defines an intercept-constant-k, $A^k$, and an at least one slope-constant-(kj), $B^k_j$:

$$Y^k_c = A^k + \Sigma_j B^k_j I^k_{jc}$$

and wherein said selection of values for said at least one constant-k comprises selecting at least one intercept-constant-k and at least one slope-constant-(kj) so that the immediately following expression is reduced substantially to its minimum value:

$$\Sigma_c (Y^i_c - A^k - \Sigma_j \{B^k_j I^k_{jc}\})^2.$$

66. The method of claim 63, wherein said calibration equation-i is in the same linear form as calibration equation-k and wherein said calibration equation-i defines dependent-variable-(ic), $Y^i_c$, in terms of at least one constant-i and at least one independent-variable-(ijc), $I^i_{jc}$, wherein said at least one constant-i comprises: an intercept-constant-i, $A^i$, and at least one slope-constant-(ij), $B^i_j$, involving each wavelength-j used in calibration equation-i; and wherein each said at least one independent-variable-(ijc), $I^i_{jc}$, has a value substantially equal to each at least one spectral feature-(ijc) determined by said first function from spectral data-(ic) measured by said instrument-i that involves each said wavelength-j for member c; and wherein said dependent-variable-(ic), $Y^i_c$, has a value substantially equal to said property-p for said sample-u when values for each said at least one constant-i and each said at least one independent-variable-(ijc) are appropriately substituted into said calibration equation-i and sample-u is member c, whereby calibration equation-i and equation-k, respectively, have the linear forms:

$$Y^i_c = A^i + \Sigma_j \{B^i_j I^i_{jc}\}$$

and $$Y^k_c = A^i + \Sigma_j \{B^i_j I^i_{jc}\};$$

and wherein the following two equations are simultaneously substantially satisfied:

$$B^k_j = B^i_j \{\Sigma_c (I^i_{jc} I^k_{jc})\} / \Sigma_c (I^k_{jc})^2$$

and $$A^k = \Sigma_c \{Y^i_c - \Sigma_j (B^k_j I^k_{jc})\} / n$$

whereby said calibration equation-k for instrument-k is obtained by reference to said calibration equation-i.

67. The method of claim 63, wherein said calibration equation-i is in the same linear form as calibration equation-k and wherein said calibration equation-i defines dependent-variable-(ic) in terms of at least one constant-i and at least one independent-variable-(ijc), wherein said at least one constant-i of calibration equation-i comprises: an intercept-constant-i, and at least one slope-constant-(ij) involving each wavelength-j used in calibration equation-i; and wherein each said at least one independent-variable-(ijc) has a value substantially equal to each at least one spectral feature-(ijc) determined by said first function from spectral data-(ic) measured by instrument-i that involves each said wavelength-j for member c, and wherein said dependent-variable-(ic) has a value substantially equal to said property-p for said sample-u when values for each said at least one constant-i and each said at least one independent-variable-(ijc) are appropriately substituted into said calibration equation-i and sample-u is member c; whereby calibration equation-i and equation-k, respectively have the linear forms:

$$Y^i_c = A^i + \Sigma_j\{B^i_j I^i_{jc}\}$$

and $$Y^k_c = A^k + \Sigma_j\{B^k_j I^k_{jc}\};$$

and wherein the following two equations are simultaneously substantially satisfied:

$$B^k_j = B^i_j \Sigma_c I^i_{jc} / \Sigma_c I^k_{jc}$$

and $$A^k = \Sigma_c\{Y^i_c - \Sigma_j(B^k_j I^k_{jc})\}/n$$

whereby said calibration equation-k for instrument-k is obtained by reference to said calibration equation-i.

68. The method of claim 63, wherein there is a further improvement of applying a slope and bias correction comprising the steps of: determining values for m and b, which substantially satisfy the following expressions simultaneously:

$$m = \{\Sigma_c Y^a_c \Sigma_c Y^k_c\}/I - \Sigma_c(Y^a_c Y^k_c)\}/\{(\Sigma_c Y^k_c \Sigma_c Y^k_c)/I - \Sigma_c Y^k_c Y^k_c\}$$

$$b = \{\Sigma_c Y^a_c - m\Sigma_c Y^k_c\}/I$$

where:
dependent-variable-(ac), $Y^a_c$, is selected from the group of values consisting of: a directly determined value for property-p of a particular member c, of sample-u; a predicted value for property-p of a particular member c, of sample-u by means of a calibration equation for property-p in a range of interest; and a combination thereof;
I is the number of members of sample-u; and to apply said slope and bias correction, substitute said values for m and b into the following expression:

$$\hat{Y}^k_c = \{mA^k + b\} + \Sigma_j\{mB^k_j I^k_{jc}\}$$

whereby an improved calibration equation-k for a slope and bias corrected dependent-variable-(kc), $Y^k_c$, for instrument-k is obtained.

69. The method of claim 63, wherein said property-p is selected from the group consisting of octane and cetane and said spectral data-k and -i, respectively, each correspond to at least one absorbance for light radiation with a frequency for each member c, in the range of about 800 to 2500 nanometers.

70. In a method of claim 63, wherein said member c is selected from the group consisting of isooctane, n-decane, 1-octene, 2,3,4-trimethylpentane, n-heptane cyclohexane, n-hexane, and toluene.

71. The method of claim 63, wherein instead of a value equal to dependent-variable-(ic) being substituted for that value for dependent-variable-(kc), a mathematically transformed dependent-variable-(ic), $Y^t_c$, by means of a function is used to yield $Y^t_c$ that is substituted for dependent-variable-(kc), $Y^k_c$, in calibration equation-k.

72. The method of claim 71, wherein said $Y^t_c$ is determined by a function selected from the group consisting of:

$Y^t_c = u \times Y^i_c + v$; $Y^t_c = u \times \log Y^i_c + v$; where u is any real number not equal to zero and v is any real number including zero.

73. The method of claim 63, wherein said first function to obtain spectral feature-(ic) and spectral feature-(kc), respectively, from spectral data-(ic) and spectral data-(kc) for each member c, comprises differentials.

74. The method of claim 73, wherein said differentials comprise at least second order.

75. The method of claim 74, wherein said wavelength-j includes at least one frequency selected from the group consisting of at least one methyne band.

76. A method for calibrating or recalibrating a first instrument, instrument-k, by reference to a second instrument, instrument-i, comprising in any order:
(a) obtaining spectral data by means of instrument-k and instrument-i, corresponding respectively to data-k and data-i for each member of a calibration set;
(b) determining by means of a calibration equation, calibration equation-i, of said instrument-i, a value, value-i, for a dependent variable, dependent variable-i, corresponding to each member of said calibration set;
(c) substituting a value, value-f, related by function-f to said value-i for said dependent variable-i, for each member of the calibration set in place of that value for said dependent variable-k in a calibration equation-k which contains constants-k and a dependent variable, dependent variable-k;
(d) selecting values for said constants-k in calibration equation-k so that the sum of absolute differences between:
(1) each dependent variable-k calculated based on said calibration-k with said selected constants-k and data-k for each member of said calibration set; and
(2) corresponding values for identical members of said calibration set determined by function-f and corresponding value-i for dependent variable-i of each said member;
is substantially minimized;
whereby said constants-k can be inversely transformed by an inverse to function-f to define calibration equation-k.

77. A method for determining constants in a calibration equation, calibration equation-1, for a first instrument by recourse to a second instrument having a calibration equation, calibration equation-2, comprising in any order:
(a) determining from calibration equation-2 a value for each dependent variable-2 corresponding to each member of a calibration set based on spectral data-2 for each member of said calibration set measured by means of instrument-2; and
(b) determining constants-1 in said calibration equation-1 so that the sum of absolute differences between:
(1) said value for each said dependent variable-2 for each member of said calibration set; and (2) that corresponding value of dependent variable-1 calculated for each said member based upon calibration equation-1;
is substantially minimized.

78. The method of claim 77, wherein said calibration set has at least one member that has spectral data-2 which in conjunction with calibration equation-2 determines a value for said dependent variable-2 for said at least one member which is significantly different from that value determined by a direct test method for which said calibration equation-1 and calibration equation-2 were established to model.

79. The method of claim 77 wherein a slope and bias adjustment is made to instrument-k's calibration equation to minimize the errors on subsequent samples.

* * * * *